United States Patent
Fang et al.

(10) Patent No.: US 9,273,137 B2
(45) Date of Patent: Mar. 1, 2016

(54) FGFR-FC FUSION PROTEINS AND THE USE THEREOF

(71) Applicant: YANTAI RC BIOTECHNOLOGIES, Shadong Province (CN)

(72) Inventors: Jianmin Fang, Yantai (CN); Dong Li, Yantai (CN)

(73) Assignee: REMEGEN, LTD., Shandong (CN)

(*) Notice: Subject to any disclaimer, the term of this patent is extended or adjusted under 35 U.S.C. 154(b) by 0 days.

(21) Appl. No.: 13/842,345

(22) Filed: Mar. 15, 2013

(65) Prior Publication Data

US 2013/0195864 A1  Aug. 1, 2013

Related U.S. Application Data

(63) Continuation-in-part of application No. PCT/CN2012/075706, filed on May 18, 2012.

(30) Foreign Application Priority Data

May 20, 2011 (CN) .................. 2011 1 01322189

(51) Int. Cl.
  C07K 16/22 (2006.01)
  C07K 14/71 (2006.01)
  A61K 47/48 (2006.01)
  A61K 38/00 (2006.01)
  C07K 16/28 (2006.01)

(52) U.S. Cl.
  CPC ....... *C07K 16/2863* (2013.01); *A61K 47/48369* (2013.01); *A61K 47/48423* (2013.01); *C07K 14/71* (2013.01); *A61K 38/00* (2013.01); *C07K 2319/30* (2013.01)

(58) Field of Classification Search
  CPC ............... C07K 14/71; C07K 2319/32; C07K 2319/30; C07K 2319/00
  See application file for complete search history.

(56) References Cited

PUBLICATIONS

Beenken, Mohommadi, "The FGF family: biology, pathophysiology and therapy", *Nature Reviews*, 8(3): 235-53, 2009, Macmillan Publishers Limited.
Casanovas et al., "Drug resistance by evasion of antiangiogenic targeting of VEGF signaling in late-stage pancreatic islet tumors", *Cancer Cell*, 8(4): 299-309, Oct. 2005, Elsevier Inc.
Eswarakumar et al., "Cellular signaling by fibroblast growth factor receptors", *Cytokine Growth Factor Reviews*, 16: 139-149, Feb. 1, 2005, Elsevier Inc.
Ferrara et al., "The biology of VEGF and its receptors", *Nature Medicine*, 9(6): 669-676, Jun. 2003.
Ferrara, "Vascular Endothelial Growth Factor as a Target for Anticancer Therapy", *The Oncologist*, 9(1): 2-10, Jan. 15, 2004.
Gauglhofer et al., "Up-Regulation of the Fibroblast Growth Factor 8 Subfamily in Human Hepatocellular Carcinoma for Cell Survival and Neoangiogenisis", *Hepatology*, 53(3): 854-864, Mar. 2011, American Association for the Study of Liver Diseases.
Hsu etal., "Monoclonal Antibodies Targeting Vascular Endothelial Growth Factor: Current Status and Future Challenges in Cancer Therapy", *Biodrugs*, 23(5): 289-304, 2009, Adis Data Information.
Hurwitz et al., "Bevacizumab plus Irinotecan, Fluorouracil, and Leucovorin for Metastatic Colorectal Cancer" *The New England Journal of Medicine*, 350(23): 2335-2342, Jun. 3, 2004, Massachusetts Medical Society.
Jenab-Walcott, Giantonio, et al., "Bevacizumab: current indications and future development for management of solid tumors", *Expert Opinion on Biological Therapy*, 9(4): 507-517, Apr. 2009 [Abstract Only].
Krupitskaya et al., "Ramucirumab, a fully human mAb to the transmembrane signaling tyrosine kinase VEGFR-2 for the potential treatment of cancer", *Current Opinion in Investigational Drugs*, 10(6): 597-605, Jun. 2010 [Abstract Only].
Mohammadi et al., "Structural basis for fibroblast growth factor receptor activation", *Cytokine & Growth Factor Reviews*, 16: 107-137, Mar. 2005, New York University School of Medicine.
Olsen et al., "Insights into the molecular basis for fibroblast growth factor receptor autoinhibition and ligand-blinding promiscuity", *Proceedings of the National Academy of Sciences of the United States of America*, 101(4): 935-940, Jan. 27, 2004.
Sandler et al., "Paclitaxel-Carboplatin Alone or with Bevacizumab for Non-Small-Cell Lung Cancer", *The New England Journal of Medicine*, 355(24): 2542-2550, Dec. 14, 2006, Massachusetts Medical Society.
Summers et al., "FDA Drug Approval Summary: Bevacizumab plus Interferon for Advances Renal Cell Carcinoma", *The Oncologist*, 15(1): 104-111, 2010.
Wang et al., "Alternately Spliced NH2-terminal Immunoglobulin-like Loop I in the Ectodomain of the Fibroblast Growth Factor (FGF) Receptor 1 Lowers Affinity for both Heparin and FGF-1", *The Journal of Biological Chemistry*, 270:10231-10235, Apr. 28, 1995, The American Society of Biochemistry and Molecular Biology, Inc.

*Primary Examiner* — Ruixiang Li
(74) *Attorney, Agent, or Firm* — Saliwanchik, Lloyd & Eisenschenk

(57) ABSTRACT

The present invention belongs to the field of biotechnology and relates to the treatment of diseases, especially the treatment of FGF overexpression-related diseases. Particularly, the present invention relates to FGFR-Fc fusion proteins and the use thereof in the treatment of angiogenesis regulation-related diseases. More particularly, the present invention relates to isolated soluble FGFR-Fc fusion proteins and their applications in manufacture of the medicament for the treatment of angiogenesis regulation-related diseases.

6 Claims, 8 Drawing Sheets

FGFR-FC FUSION PROTEINS AND THE USE THEREOF

CROSS-REFERENCE TO A RELATED APPLICATION

The present application is a continuation-in-part of International Application PCT/CN2012/075706, filed May 18, 2012; which claims priority to Chinese Application No. 2011 10132218.9, filed May 20, 2011; both of which are incorporated by reference herein in their entirety, including any figures, tables, nucleic acid sequences, amino acid sequences, or drawings.

The Sequence Listing for this application is labeled "SeqList-10 Jun. 14-ST25.txt which was created on Jun. 10, 2014 and is 105 KB. The entire content of the sequence listing is incorporated herein by reference in its entirety.

FIELD OF THE INVENTION

The present invention belongs to the field of biotechnology and relates to the treatment of diseases, especially the treatment of FGF overexpression-related diseases. Particularly, the present invention relates to FGFR-Fc fusion proteins and the use thereof in the treatment of angiogenesis regulation-related diseases. More particularly, the present invention relates to isolated soluble FGFR-Fc fusion proteins and their applications in manufacture of the medicament for the treatment of angiogenesis regulation-related diseases.

BACKGROUND OF THE INVENTION

Angiogenesis is one of the primary factors resulting in the growth and metastasis of malignant tumors [1]. The process of angiogenesis is regulated by many factors, among which some factors promote angiogenesis, while some factors inhibit angiogenesis, and as a result, the regulation of angiogenesis is a very complicated dynamic process [2]. Anti-angiogenesis treatment is intended to control the growth of a tumor by blocking angiogenic stimulating factors or preventing angiogenesis in the tumor using angiogenesis inhibitors. At present, a large amount of angiogenic stimulating factors are known, such as, for example, vascular endothelial growth factor (VEGF), fibroblast growth factor (FGF), hepatocyte growth factor (HGF) etc. which may stimulate the division and differentiation of vascular endothelial cells and the morphogenesis of blood vessels. Among these factors mentioned above, it is now known that VEGF is the most angiogenesis-specific and the most effective growth factor [3, 4].

In a hypoxic environment inside tumor tissue, VEGFs are secreted by the tumor cells, which induce the division and migration of vascular endotheliocytes, resulting in the establishment of a tumor vascular network. It has been demonstrated that the inhibition of VEGF may prevent angiogenesis, and further inhibit the growth of tumor. For this reason, VEGF and its receptors are important targets for anti-angiogenesis medicaments.

At present, anti-angiogenesis medicaments demonstrated in clinical trials to have efficacy include Bevacizumab (under the trade name of Avastin), which is able to block VEGF directly and inhibit the tumor angiogenesis. Bevacizumab was approved for marketing by the FDA in 2004, and as a first-line drug for rectal cancer, it is the first marketing-approved drug that plays a role in anticarcinogenesis by inhibiting angiogenesis. Avastin is a humanized anti-VEGF monoclonal antibody, which is produced by Genentech. In a large-scale Phase III clinical trial, the combined therapy by Avastin and chemotherapy may significantly extend the survival time of the patients suffered from many kinds of cancers, including rectal cancer, lung cancer, breast cancer and renal cancer. [5, 6] The clinical success of Avastin is a landmark, demonstrating that the anti-angiogenesis treatment using tumor vascular system as the target is a clinically effective measure and provide a new path for the tumor treatment.

Besides Avastin, several drugs for anti-VEGF signaling are also in the late phase of human clinical trial and are expected for clinical application in the next several years. Among others, Aflibercept (also called as VEGF-Trap), developed by the Regeneron and Sanofi-Aventis, is now in Phase III clinical trial[7]. An anti-VEGF receptor II (VEGFR2) monoclonal antibody drug IMC-1121B (Imclone) is also in Phase III clinical trial[8]. The amino acid sequence of VEGFR2 is provided in SEQ ID NO: 3 and the nucleotide sequence of VEGFR2 mRNA is provided in SEQ ID NO: 6.

Great progress has been achieved in the clinical treatment of tumor using anti-VEGF medicament, however, it has also been shown by the clinical trial that the anti-VEGF treatment are also considerably limited. From the point of the effect of tumor treatment, Avastin may extend the half survival time of the colon cancer patient for about 3-4 months [9, 10], and extend the half survival time of the breast cancer patient for about 7-8 months [11], and thus, Avastin cannot effectively inhibit the growth of tumor blood vessel over the long term.

The primary causes resulting in the failure of anti-VEGF treatment or the appearance of resistance may depend on the regulation of tumor angiogenesis by a plurality of factors. Although VEGF plays an important role in angiogenesis, it is not the only angiogenesis stimulating factor. Meanwhile, owing to the heterogeneity of tumor cells, the complexity of tumor microenvironment and the compensatory response mechanism of body, when the activity of VEGF is inhibited for a long period of time, other angiogenesis stimulating factors would be expressed [12], and thus the growth of tumor blood vessel is no longer dependent on VEGF signaling path.

The variation of angiogenesis factors expressed by the tumor was studied during anti-VEGFR2 treatment for pancreatic tumor by Prof Hanahan's group (University of California, San Francisco, US), indicating that the expression of several genes changed during anti-VEGF treatment, in which the expression of FGF-2 significantly increased. It has been shown that the expression of FGF, especially FGF-2, increased significantly in the tumor resistant to anti-VEGF treatment so that angiogenesis was activated again and the tumor repopulation was inhibited after blocking FGF signal pathway [13]. It may be seen that the over-expression of FGF-2 is closely related to the ability of tumor to escape from anti-VEGF treatment.

Fibroblast growth factor (FGF) is a growth factor family for heparin-binding, and there are 22 family members (FGF 1-14, 16-23) in mammals. FGF plays an important role in many biological functions, for example, cell proliferation, differentiation, migration, angiogenesis and tumorigenesis. Fibroblast growth factor receptor (FGFR) is the receptor that binds the family members of fibroblast growth factor. FGF may bind FGFR and activate the downstream signal pathway, which plays an important role in a physiological and pathological process, such as embryogenesis, development, vasculogenesis, vasodilatation, neuroregulation, ischemia protection, wound healing and tumorigenesis. [14, 15] It has been demonstrated that overexpression of FGF/FGFR in vivo is closely related to many diseases including tumors (such as fibroma, neuroglioma, melanoma, prostate carcinoma, lymphomata, leukaemia, urinary, and system cancer), skeletal system diseases (dwarfism, craniosynostosis, achondroplasia, and acanthosis nigricans) and renal failure. It has been reported that increased expression level of FGF and its receptor may directly promote the survival and proliferation of tumor cells, and the survival of hepatic carcinoma cells is significantly reduced by down-regulation of FGF by siRNA [22].

At present, few researches focus on the development of new anti-angiogenesis medicament using FGF and its receptor as the target in clinical trials. For example, FP-1039, a fusion protein composed of whole extracellular domain of human FGFR1 and human IgG1 Fc fragment, is developed by a US company Five Prime and now in volunteer recruitment stage of Phase I clinical trail. However, it has been suggested by researches of Wang and Olsen that the first Ig-like domain of the extracellular domain of human FGFR1 and the linking fragment between the first and the second Ig-like domain of the extracellular domain of human FGFR1 may inhibit binding of FGFR1 and FGF [20, 21].

The tertiary structure of a protein is closely related to its biological function. The FGF binding capacity is directly influenced differences among the conformations of each Ig-like domain of the extracellular domain of FGFR and the linking fragment. Different fusion proteins, composed of the FGFR extracellular domain fragments of various lengths and IgG Fc, are constructed by means of genetic engineering to obtain fusion proteins with different conformations, so that the fusion protein with high efficiency of FGF binding and biological activity can be screened.

There are four FGFR genes in mammals: fgfR1-fgfR4. Fibroblast growth factor receptor is composed of the extracellular domain, transmembrane domain and intracellular domain. There are many members in FGFR family, which have similar extracellular domain but vary in the ligand binding property and kinase domain. Their extracellular domains include three immunoglobulin-like (Ig-like) domains: the first Ig-like domain, the second Ig-like domain and the third Ig-like domain, and there is a sequence between the first and the second Ig-like domain, which is referred as the intermediate functional sequence of the Ig-like domain of FGFR (IFS for short herein) in this specification. The intermediate functional sequence may comprise one acidic amino acid segment, which is referred as acidic box (AB).

BRIEF SUMMARY

The present invention provides isolated soluble fusion proteins of fibroblast growth factor receptor (FGFR), which comprise: a part derived from an intermediate functional sequence (also referred to herein as IFS) of an Ig-like domain of FGFR, a second Ig-like domain (also referred to herein as D2) of FGFR, a third ig-like domain (also referred to herein as D3) of FGFR and an immunoglobulin Fc region.

In certain embodiments, the part derived from IFS contains no acidic box. In other embodiments, the IFS portion has the amino acid sequence of position 134 to position 162, position 145 to position 162, or position 151 to position 162 of SEQ ID NO: 1, or has an amino acid sequence sharing at least 70% identity with the amino acid sequence of position 134 to position 162, position 145 to position 162 or position 151 to position 162 of SEQ ID NO: 1.

The present invention further relates to a fusion protein, which comprises or consists of: the first Ig-like domain (also referred to herein as D1) of FGFR or a moiety thereof, a part derived from the intermediate functional sequence region of the Ig-like domain of FGFR, the second Ig-like domain of FGFR, the third Ig-like domain of FGFR, and an immunoglobulin Fc region.

Preferably, the D1 domain or a moiety thereof possesses:

the amino acid sequence corresponding to position 40 to position 118 of SEQ ID NO: 1, or an amino acid sequence sharing at least 70% identity, preferably at least 80%, 90%, 93%, 95%, 97%, 98% or 99% identity with the sequence of position 40 to position 118 of SEQ ID NO: 1; or the amino acid sequence corresponding to position 77 to position 118 of SEQ ID NO: 1, or an amino acid sequence sharing at least 70% identity, preferably at least 80%, 90%, 93%, 95%, 97%, 98% or 99% identity with the amino acid sequence of position 77 to position 118 of SEQ ID NO:1.

In one aspect, the present invention provides a fusion protein that comprises or consists of: the intermediate functional sequence region of the Ig-like domain of FGFR or a moiety thereof, the second Ig-like domain of FGFR, the third Ig-like domain of FGFR and immunoglobulin Fc region, wherein:

the second Ig-like domain of FGFR has the amino acid sequence corresponding to position 163 to position 247 of SEQ ID NO: 1, or an amino acid sequence sharing at least 70% identity, preferably at least 80%, 90%, 93%, 95%, 97%, 98% or 99% identity with the amino acid sequence of position 163 to position 247 of SEQ ID NO: 1; and/or the third Ig-like domain of FGFR has the amino acid sequence corresponding to position 270 to position 359 of SEQ ID NO: 1, or an amino acid sequence sharing at least 70% identity, preferably at least 80%, 90%, 93%, 95%, 97%, 98% or 99% identity with the amino acid sequence of position 270 to position 359 of SEQ ID NO: 1.

The present invention further provides a fusion protein that comprises a region derived from the extracellular domain of FGFR and a immunoglobulin Fc region or composed thereof, wherein the region derived from the extracellular domain of FGFR:

(1) has the amino acid sequence indicated by positions 358-580 of SEQ ID NO: 9, positions 304-526 of SEQ ID NO: 10, positions 278-500 of SEQ ID NO: 11, positions 246-468 of SEQ ID NO: 12, positions 235-457 of SEQ ID NO: 13, positions 229-451 of SEQ ID NO: 14 or positions 224-446 of SEQ ID NO: 15, or the amino acid sequence encoded by the nucleotide sequence indicated by positions 1074-1740 of SEQ ID NO: 16, positions 912-1578 of SEQ ID NO: 17, positions 834-1500 of SEQ ID NO: 18, positions 738-1404 of SEQ ID NO: 19, positions 705-1371 of SEQ ID NO: 20, positions 687-1353 of SEQ ID NO: 21 and positions 672-1338 of SEQ ID NO: 22;

(2) comprises or consists of the amino acid sequence sharing at least 70% identity, preferably at least 80%, 90%, 93%, 95%, 97%, 98% or 99% identity with the amino acid sequence indicated by positions 358-580 of SEQ ID NO: 9, positions 304-526 of SEQ ID NO: 10, positions 278-500 of SEQ ID NO: 11, positions 246-468 of SEQ ID NO: 12, positions 235-457 of SEQ ID NO: 13, positions 229-451 of SEQ ID NO: 14 or positions 224-446 of SEQ ID NO: 15; or (3) comprises or consists of the amino acid sequence encoded by a nucleotide sequence sharing at least 70% identity, preferably at least 80%, 90%, 93%, 95%, 97%, 98% or 99% identity with the nucleotide sequence indicated by positions 1074-1740 of SEQ ID NO: 16, positions 912-1578 of SEQ ID NO: 17, positions 834-1500 of SEQ ID NO: 18, positions 738-1404 of SEQ ID NO: 19, positions 705-1371 of SEQ ID NO: 20, positions 687-1353 of SEQ ID NO: 21 or positions 672-1338 of SEQ ID NO: 22.

The present invention further relates to a fusion protein, wherein the protein:

(1) comprises the amino acid sequence indicated by any one of SEQ ID NOs: 9-15, or an amino acid sequence encoded by the nucleotide sequence indicated by any one of SEQ ID NOs: 16-22;

(2) comprises or consists of the amino acid sequence sharing at least 70% identity, preferably at least 80%, 90%, 93%, 95%, 97%, 98% or 99% identity, with the amino acid sequence indicated by any one of SEQ ID NOs: 9-15; or (3) comprises or consists of the amino acid sequence encoded by the nucleotide sequence sharing at least 70% identity, preferably at least 80%, 90%, 93%, 95%, 97%, 98% or 99% identity, with the nucleotide sequence indicated by any one of SEQ ID NOs: 16-22.

Preferably, in the fusion protein of the present invention, the immunoglobulin Fc region is human IgG1 Fc region, and more preferably, it comprises:

the amino acid sequence corresponding to SEQ ID NO: 7, or the amino acid sequence sharing at least 70% identity, preferably at least 80%, 90%, 93%, 95%, 97%, 98% or 99% identity, with the amino acid sequence of SEQ ID NO: 7; or the amino acid sequence encoded by the nucleotide sequence corresponding to SEQ ID NO: 8, or the amino acid sequence encoded by the nucleotide sequence sharing at least 70% identity, preferably at least 80%, 90%, 93%, 95%, 97%, 98% or 99% identity, with the nucleotide sequence of SEQ ID NO: 8.

In one embodiment of the present invention, the immunoglobulin Fc region is located at the C-terminus of the fusion protein.

The present invention further provides a fusion protein precursor comprising a secretory signal peptide region, for example, VEGFR1 signal peptide region, and preferably, the secretory signal peptide region has the amino acid sequence of position 1 to position 26 of SEQ ID NO: 2 or the amino acid sequence encoded by the nucleotide sequence of SEQ ID NO: 23. Preferably, the signal peptide region is located at the N-terminus of the precursor. The nucleotide sequence of VEGFR1 mRNA is provided in SEQ ID NO: 5.

In another aspect of the present invention, an isolated nucleic acid molecule that encodes the fusion protein or the precursor of the fusion protein of the present invention is provided. Preferably, the nucleic acid molecule comprises the nucleotide sequence indicated by any one of SEQ ID NOs: 16-22.

The present invention provides a fusion protein that sequentially comprises from the N-terminus to the C-terminus: portions derived from IFR, D2, D3 and immunoglobulin Fc region.

The domains and/or regions involved in the fusion protein of the present invention can be linked directly and/or by a linker. In one embodiment, the region derived from the extracellular domain of FGFR and immunoglobulin Fc region are linked directly. In another embodiment, the region derived from the extracellular domain of FGFR and immunoglobulin Fc region are linked by a linker.

In one aspect, the fusion protein of the present invention inhibits angiogenesis. In another aspect, the fusion protein of the present invention binds FGF, preferably FGF2, in vivo and/or in vitro. In another aspect, the fusion protein of the present invention inhibits tumor cells directly.

The present invention further relates to an FGFR-Fc fusion protein that comprises a portion derived from the extracellular domain of FGFR and a portion derived from immunoglobulin Fc region. Particularly, the portion derived from the extracellular domain of FGFR is derived from the extracellular domain of FGFR1. Preferably, the immunoglobulin Fc region is a human immunoglobulin Fc region, for example, a human IgG1 Fc region. In one aspect of the present invention, the FGFR-Fc fusion protein of the present invention has the capacity of binding and/or antagonizing FGF, and thus, inhibit angiogenesis.

In the FGFR-Fc fusion protein of the present invention, the portion derived from the extracellular domain of FGFR may comprise one or more selected from the group consisting of: D1 domain or a moiety thereof, the portion derived from IFS, D2 domain or a moiety thereof and D3 domain or a moiety thereof.

In one embodiment, the part derived from the extracellular domain of FGFR may comprise D1 or a moiety thereof, the part derived from IFS, D2 domain and D3 domain.

In another embodiment, the part derived from the extracellular domain of FGFR may comprise the part derived from IFS, D2 domain and D3 domain, and preferably, the part derived from IFS has the amino acid sequence corresponding to position 134 to position 162, position 145 to position 162, or position 151 to position 162 of SEQ ID NO: 1.

In some embodiments, the FGFR-Fc fusion protein of the present invention contains no D1 or a moiety thereof. In some other embodiments, the FGFR-Fc fusion protein of the present invention contains no part from IFS other than the amino acid sequence corresponding to position 134 to position 162, position 145 to position 162, or position 151 to position 162 of SEQ ID NO: 1.

In some embodiments of the present invention, the order from the N-terminus to the C-terminus of each region and/or each domain involved in the FGFR-Fc fusion protein may be any order. In some other embodiments, the order can be as shown in FIG. 1. In some other embodiments, the order may be different from the order shown in FIG. 1.

In some embodiments, the FGFR-Fc fusion protein of the present invention further comprises one or more intrachain disulfide bonds, and preferably, comprises one or more intrachain disulfide bonds in the Ig-like domain.

In one aspect of the present invention, the FGFR-Fc fusion protein can be produced by expression of the nucleic acid comprising the nucleotide sequence indicated by any one of SEQ ID NOs: 16-22 in a mammalian cell line. The mammalian cell line can be, for example, a CHO cell line.

In another aspect of the present invention, a vector comprising the nucleic acid molecule of the present invention is provided.

In another aspect of the present invention, cells, such as CHO cells, transfected by the vector are provided.

In another embodiment of the present invention, a pharmaceutical composition, which comprises the fusion protein, the nucleic acid molecule, the vector, or the cells of the present invention, as well as a pharmaceutically acceptable carrier, is also provided.

In another aspect, the present invention provides a method for producing the angiogenesis-inhibitory fusion protein, which is carried out by expressing the fusion protein of the present invention in prokaryotic cells or eukaryotic cells, especially, in mammalian cell lines.

The present invention further provides a method for producing the angiogenesis-inhibitory fusion protein, which is carried out by expressing the nucleic acid molecule of the present invention in a mammalian cell. The mammalian cell line can be, for example, a CHO cell line.

In another aspect of the present invention, a method for inhibition of angiogenesis is provided, which comprises administering, to a subject in need thereof, an angiogenesis-inhibiting effective amount of the FGFR-Fc fusion protein, the nucleic acid molecule encoding the protein, the vector comprising the nucleic acid molecule and/or a pharmaceutical composition comprising any one of these materials. Preferably, the method is carried out in a mammal.

In another aspect of the present invention, a method for the treatment and/or prevention of a tumor in a mammal is provided. This method comprises administering, to a need of such treatment, a therapeutically or preventively effective amount of the FGFR-Fc fusion protein, the nucleic acid molecule encoding the protein, the vector comprising the nucleic acid molecule, and/or a pharmaceutical composition comprising any one of these materials. Preferably, the tumor is a solid tumor.

In another aspect, the present invention provides a method for the treatment or prevention of ophthalmic angiogenesis-related diseases in mammals. This method comprises administering, to a subject in need of such treatment or prevention, a therapeutically or preventively effective amount of the FGFR-Fc fusion protein, the nucleic acid molecule encoding the protein, the vector comprising the nucleic acid molecule, and/or a pharmaceutical composition comprising any one of these materials. Preferably, the ophthalmic angiogenesis-related disease is age-related macular degeneration.

The present invention further relates to use of the FGFR-Fc fusion protein, the nucleic acid molecule encoding the protein, the vector comprising the nucleic acid molecule, and/or a pharmaceutical composition comprising any one mentioned above according to the present invention in the manufacture of a medicament for inhibiting angiogenesis.

Furthermore, the present invention further relates to use of the FGFR-Fc fusion protein, the nucleic acid molecule encoding the protein, the vector comprising the nucleic acid molecule, and/or a pharmaceutical composition comprising any one mentioned above according to the present invention in manufacture of a medicament for the treatment or prevention of angiogenesis-related diseases, and preferably, the angiogenesis-related disease is a tumor or ophthalmic angiogenesis-related disease.

In the disclosure, only some specific embodiments claimed for protection are illustrated by way of example, in which the technical features described in one or more technical proposals can be combined with any one or more technical proposals, and these technical proposals obtained by combination are also within the scope of this application, as if these technical proposals obtained by combination were already specifically described in the disclosure.

It should be understood that the description below is only illustrated by way of example for the technical solutions claimed for protection by the present invention, and not regarded as any limitation on these technical solutions. The protection scope of the present invention shall be defined by the claims as appended.

BRIEF DESCRIPTION OF THE SEQUENCES

Figure 1:
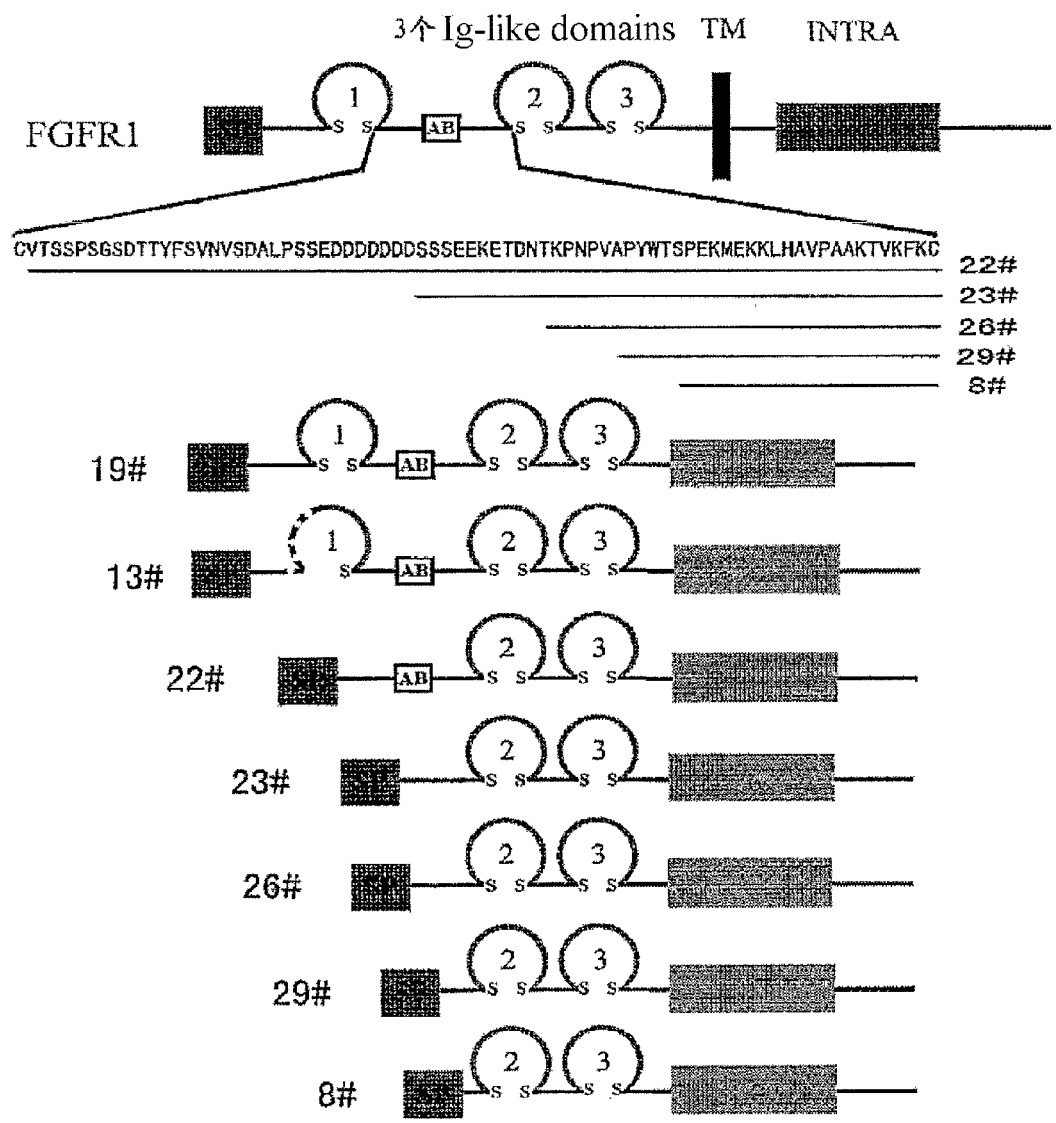
FIG. 1 is a structural representation of a FGFR1-Fc fusion protein. The FGFR1-Fc fusion protein is represented by a solid line, and a deleted amino acid is represented by a dashed line; the antibody-like domain is represented by a circle; different antibody-like domains are represented by numbers 1-3; a disulfide bond is represented by s s; human IgG1 Fc is represented by a grey box; VEGFR1 signal peptide is represented by SP; the acidic box sequence is represented by a box with the letters AB.

SEQ ID NO:1 is an amino acid sequence of human FGRF1.
SEQ ID NO:2 is an amino acid sequence of human VEGFR1.
SEQ ID NO:3 is an amino acid sequence of human VEGFR2.
SEQ ID NO:4 is a nucleotide sequence of human FGFR1.
SEQ ID NO:5 is a nucleotide sequence of human VEGFR1.
SEQ ID NO:6 is a nucleotide sequence of human VEGFR2.
SEQ ID NO:7 is an amino acid seq of human IgG Fc.
SEQ ID NO:8 is a DNA seq of human IgG Fc.
SEQ ID NO:9 is a #19 fusion protein.
SEQ ID NO:10 is a #13 fusion protein.
SEQ ID NO:11 is a #22 fusion protein.
SEQ ID NO:12 is a #23 fusion protein.
SEQ ID NO:13 is a #26 fusion protein.
SEQ ID NO:14 is a #29 fusion protein.
SEQ ID NO:15 is a #8 fusion protein.
SEQ ID NO:16 is a DNA seq of #19 fusion protein.
SEQ ID NO:17 is a DNA seq of #13 fusion protein.
SEQ ID NO:18 is a DNA seq of #22 fusion protein.
SEQ ID NO:19 is a DNA seq of #23 fusion protein.
SEQ ID NO:20 is a DNA seq of #26 fusion protein.
SEQ ID NO:21 is a DNA seq of #29 fusion protein.
SEQ ID NO: 22 is a DNA seq of #8 fusion protein.
SEQ ID NO:23 is a DNA seq of VEGFR1 signal peptide.
SEQ ID NO:24 is a forward primer DNA seq of #19 fusion protein.
SEQ ID NO:25 is a forward primer of DNA seq of #13 fusion protein.
SEQ ID NO:26 is a forward primer DNA seq of #22 fusion protein.
SEQ ID NO:27 is a forward primer DNA seq of #23 fusion protein.
SEQ ID NO:28 is a forward primer DNA seq of #26 fusion protein.
SEQ ID NO:29 is a forward primer DNA seq of #29 fusion protein.
SEQ ID NO:30 is a forward primer DNA seq of #8 fusion protein.
SEQ ID NO:31 is a reverse primer DNA seq of FGFR1.
SEQ ID NO: 32 is a forward primer DNA seq of human IgG Fc.
SEQ ID NO:33 is a reverse primer DNA seq of human IgG Fc.

DETAILED DESCRIPTION

Definitions

Unless otherwise defined, all scientific terms used herein have the same meaning as commonly understood by those skilled in the art. With regard to the definitions and terms in the art, reference may be made to Current Protocols in Molecular Biology (Ausubel) by the skilled one. Standard three- and/or one-letter code used for expressing one of 20 common L-amino acids in the art are adopted as the abbreviation of amino acid residues.

Although the number ranges and approximate parameter values are given in a broad range in the present invention, all numbers in the specific examples are described as precise as possible. However, certain errors can exist in any numerical values, which may result from, for example, the standard deviation during the measurement. Additionally, all ranges disclosed herein encompass any and all possible subranges contained therein. For example, it should be understood that the range "from 1 to 10" as described herein encompasses any and all possible subranges between the minimum 1 and the maximum 10 (including the endpoints). Additionally, it should be understood that any reference referred as "incorporated herein" is incorporated in its entirety.

Additionally, it should be noted that unless otherwise clearly and explicitly stated, the singular form includes the plural referent, as used in the present invention. The term "or" and the term "and/or" are used interchangeably, unless otherwise clearly indicated in the context.

As used herein, the term "Fc", "Fc region", "Fc fragment" or "immunoglobulin Fc region" refers to the crystallizable fragment of immunoglobulin, and in the present invention, said Fc region is preferably the human IgG1 Fc region.

The term "Fc fusion protein" refers to the antibody-like molecule that incorporates the binding specificity of a heterologous protein and the effector function of a constant region of an immunoglobulin. In terms of the molecular structure, a Fc fusion protein comprises the amino acid sequence having the required binding specificity and the sequence of a constant region of an immunoglobulin. A Fc fusion protein molecule generally comprises a binding site of a receptor or a ligand. The sequence of immunoglobulin constant region may be derived from any immunoglobulin, for example, IgG-1, IgG-2, IgG-3 or IgG-4 subtype, IgA (including IgA-1 and IgA-2), IgE, IgD or IgM.

The term "soluble" protein as used herein refers to a protein that may be dissolved in an aqueous solution at a biologically relevant temperature, pH level and osmotic pressure. The "soluble fusion protein" as used herein is intended to mean that the fusion protein does not contain a transmembrane region or an intracellular region.

As used herein, the term "isolated" refers to a substance and/or entity that: (1) is isolated from at least some components which is present when initially produced (in natural environment and/or in an experiment device) and related thereto and/or (2) is produced, prepared and/or manufactured artificially. The isolated substance and/or entity may be isolated from at least about 10%, about 20%, about 30%, about 40%, about 50%, about 60%, about 70%, about 80%, about 90%, about 95%, about 98%, about 99%, substantially 100% or 100% other components related to it initially.

The terms "part," "fragment," or "portion" interchangeably refer to a part of polypeptide, nucleic acid or other molecular constructs.

The term "Ig-like domain" as used herein refers to immunoglobulin-like domain, which may be found in a plurality of protein families and involved in many biological functions, including cell-cell recognition, cell surface receptor, immune function and the like.

Fibroblast growth factor (FGF) is a heparin-binding growth factor family that has 22 family members in mammals (FGF 1-14, 16-23). FGF is involved in many important biological functions, such as cell multiplication, differentiation, migration, angiogenesis and tumorigenesis. FGF exerts many biological functions by binding and activating the cell surface FGF receptor (FGFR). (See, for example, Eswarakumar et al. *Cytokine Growth Factor Rev.* 16: 139-149, 2005).

Fibroblast growth factor receptor (FGFR) is the receptor that binds the family members of fibroblast growth factor. A part of fibroblast growth factor receptor is involved in the disease process. In mammals, there are 4 FGFR genes: fgfR1-fgfR4. The fibroblast growth factor receptor is composed of an extracellular domain, transmembrane domain, and intracellular domain. The members in FGFR family can differ from each other in the term of ligand binding properties and kinase domains. However, the extracellular domains thereof are similar. There are three immunoglobulin-like (Ig-like) domains contained in their extracellular domains: the first Ig-like domain, the second Ig-like domain and the third Ig-like domain, and there is also a sequence contained between the first and the second Ig-like domain. The sequence contained between the first and the second Ig-like domain is referred to herein as the intermediate functional sequence region of the Ig-like domain of FGFR. Said intermediate regulation sequence comprises a region of acidic amino acids, referred as the acidic box (AB).

As used herein, the term "the first Ig-like domain of FGFR" or "the first Ig-like domain" refers to the first Ig-like domain in the protein FGFR from the N-terminus, which has, for example, the amino acid sequence corresponding to position 40 to position 118 of SEQ ID NO: 1. Similarly, the term "the second Ig-like domain of FGFR" or "the second Ig-like domain" refers to the second Ig-like domain in the protein FGFR from the N-terminus, which has, for example, the amino acid sequence corresponding to position 163 to position 247 of SEQ ID NO: 1; the term "the third Ig-like domain of FGFR" or "the third Ig-like domain" refers to the first Ig-like domain in the protein FGFR from the N-terminus, which has, for example, the amino acid sequence corresponding to position 270 to position 359 of SEQ ID NO: 1.

Preferably, the FGFR is FGFR1, and the first Ig-like domain of FGFR is the first Ig-like domain of FGFR1, and the second Ig-like domain of FGFR is the second Ig-like domain of FGFR1, and the third Ig-like domain of FGFR is the third Ig-like domain of FGFR1.

A part of sequence of hFGFR1 is given as follows, in which each Ig-like domain is shown in shaded area sequentially, see GenBank AAH15035.1

MWSWKCLLFWAVLVTATLCTARPSPTLPEQAQPWGAPVEVESFLVHPGDLLQLRCRLR

DDVQSINWLRDGVQLAESNRTRITGEEVEVQDSVPADSGLYACVTSSPSGSDTTYFSVN

VSDALPSSEDDDDDDDSSSEEKETDNTKPNPVAPYWTSPEKMEKKLHAVPAAKTVKFK

CPSSGISQTPNPTLRWLKNGKEFKPDHRIGGYKVRYATWSIIMDSVVPSDKGNYTCIVEN

EYGSINHTYQLDVVERSPHRPILQAGLPANKTVALGSNVEFMCKVYSDPQPHIQWLKHI

EVNGSKIGPDGNDLPYVQILKTAGVNTTDKEMEVLHLRNVSFEDAGEYTCLAGNSIGLS

HHSAWLTVLEALEER

The amino acid sequence of FGFR1 may be found in SEQ ID NO: 1, and its encoding nucleotide sequence may be found in SEQ ID NO: 4.

As used herein, the term "the intermediate functional sequence region of the Ig-like domain of FGFR" or "the intermediate functional sequence of the Ig-like domain of FGFR" or "IFS" refers to the sequence between the first Ig-like domain and the second Ig-like domain in the protein FGFR, and preferably, IFS sequence has the amino acid sequence corresponding to position 118 to position 162 of SEQ ID NO: 1.

Unexpectedly, in accordance with the present invention, it has been found that there is a significant effect of the intermediate functional sequence region on the function of the Ig-like domain. In some embodiments of the present invention, the part derived from the intermediate functional sequence region contains no acidic box. More preferably, the part derived from IFS has the amino acid sequence corresponding to position 134 to position 162, position 145 to position 162, or position 151 to position 162 of SEQ ID NO: 1.

The protein FGFR is preferably FGFR1 (SEQ ID NO: 1), especially the protein FGFR1. The amino acid sequence of the human FGFR1 is shown in SEQ ID NO: 1, and its cDNA sequence is shown in SEQ ID NO: 4.

The term "FGFR" as used herein refers to fibroblast growth factor receptor, which may be FGFR1, FGFR2, FGFR3 and/or FGFR4. Preferably, the FGFR of the present invention is FGFR1, more preferably, human FGFR1.

As used herein, the term "degenerate variant" means that the degenerate variant comprises a degenerate change at the third position of the amino acid codon so that degenerate variants encode the same amino acid, for example the wobble position of a triplet code comprising one or more changed variants (also referred as synonymous variant).

As used herein, the term "subject" refers to mammals, such as humans. It also includes other animals, including domesticated animals (such as dogs and cats), livestock (such as cattle, sheep, pigs and horses) or experimental animals (such as monkeys, rats, mice, rabbits and guinea pigs).

As used herein, the term "percentage identity," "homology," or "identity" referred to the sequence identity between two amino acid sequences or nucleic acid sequences. The percentage identity may be determined by alignment between two sequences, and the percentage identity refers to the amount of the same residue (i.e., amino acid or nucleotide) at the same position in the aligned sequences. Sequence alignment and comparison may be performed using standard algorithms in the art (for example Smith and Waterman, 1981, Adv. Appl. Math. 2: 482; Needleman and Wunsch, 1970, J. Mol. Biol. 48: 443; Pearson and Lipman, 1988, Proc. Natl. Acad. Sci., USA, 85: 2444) or by the computerized versions of these algorithms (Wisconsin Genetics Software Package Release 7.0, Genetics Computer Group, 575 Science Drive, Madison, Wis.). Computerized versions that are publicly available include BLAST and FASTA. Additionally, ENTREZ available through National Institutes of Health (Bethesda Md.) may be used for sequence alignment. When BLAST and GAP-BLAST are used, default parameters for each program (for example, BLASTN, available on the website of National Center for Biotechnology Information) may be used. In one embodiment, the percentage identity between two sequences may be determined using GCG with a gap-weight of 1 so that the giving weight of each amino acid gap seems as if it is a single amino acid mismatch between two sequences. Alternatively, ALIGN (version 2.0), which is a part of GCG (Accelrys, San Diego, Calif.) Sequence Alignment Software Package, may be used.

As used herein, the term "hybridization" refers to the process by which a stable double-stranded polynucleotide is formed by non-covalent bonding between two single stranded polynucleotides. The term "hybridization" also may refer to triple-stranded hybridization. The double stranded polynucleotide (generally) produced is the "hybrid" or "duplex". "The condition for hybridization" generally includes a salt concentration lower than about 1 M, and more generally, lower than about 500 mM, and lower than about 200 mM. The hybridization temperature may be as low as 5° C., but it usually higher than about 22° C., and more usually higher than about 30° C., and preferably higher than about 37° C. Hybridization is usually carried out under strict conditions (i.e., the conditions under which the probe will hybridize to its target sequence). Strict hybridization conditions are dependent on the sequence and will be varied under different conditions. Higher hybridization temperature will be probably required by longer segments for specific hybridization. Since the hybridization stringency may be influenced by other factors (including base composition and length of the complementary strand, the presence of organic solvent and the degree of base mismatch), the combination of parameters is more important than the absolute value of any single parameter. Generally, the strict condition is selected as 5° C. lower than the Tm of the sequence under certain ionic strength and pH. Exemplary strict conditions include pH 7.0 to 8.3, sodium ion (or other salts) concentration of at least 0.01 M to no more than 1 M and temperature of at least 25° C. For strict conditions, see, for $2^{nd}$ example Sambrook, Fritsche and Maniatis. "Molecular Cloning A laboratory Manual", edition, Cold Spring Harbor Press (1989) and Anderson "Nucleic Acid Hybridization", $1^{st}$ edition, BIOS Scientific Publishers Limited (1999), which are incorporated herein by reference for all purposes mentioned above.

As used herein, the terms "linker," "peptide linker," "linking sequence," and "linker sequence" refer to a short amino acid sequence by which individual domain and/or region involved in the present fusion protein are linked together. The length of the short amino acid sequence is generally 1-20 amino acids, and preferably, 2-10 amino acids.

As used herein, the term of "the amino acid sequence corresponding to SEQ ID NO: N" in a fusion protein or part or domain means that the fusion protein or part or domain has the amino acid sequence substantially as indicated by SEQ ID NO: N, and preferably, containing no more than 1, 2, 3, 4, 5, 10 or 20 substitutions, additions, and/or deletions of amino acids, and preferably, the fusion protein or part or domain shares at least 70%, 80%, 90%, 93%, 95%, 97%, 98% or 99% identity with the amino acid sequence of SEQ ID NO: N, and more preferably, said fusion protein or part or domain has the amino acid sequence as indicated by SEQ ID NO: N.

As used herein, the term "FGFR-Fc fusion protein" refers to a fusion protein that comprises the part derived from the extracellular domain of FGFR and the part derived from the immunoglobulin Fc region, wherein the part derived from the extracellular domain of FGFR may: (1) comprise the amino acid sequence sharing at least 70% identity, preferably at least 80%, 90%, 93%, 95%, 97%, 98% or 99% identity, with the amino acid sequence indicated by any one of SEQ ID NOs: 9-15 or composed thereof; (2) comprise the amino acid sequence encoded by the nucleotide sequence sharing at least 70% identity, preferably at least 80%, 90%, 93%, 95%, 97%, 98% or 99% identity, with the nucleotide sequence indicated by any one of SEQ ID NOs: 16-22 or composed thereof; or (3) possess the amino acid sequence indicated by any one of SEQ ID NOs: 9-15, or the amino acid sequence encoded by the nucleotide sequence indicated by any one of SEQ ID NOs: 16-22.

In some preferable embodiments, the FGFR-Fc fusion protein may be encoded by a nucleic acid, in which the nucleotide sequence encoding the part derived from the extracellular domain of FGFR comprises the sequence of which a complementary sequence is hybridized with the nucleotide sequence as indicated by any one of SEQ ID NOs: 16-22 under stringent conditions, or comprises a degenerative variant of the nucleotide sequence as indicated by any one of SEQ ID NOs: 16-22. In some preferable embodiments, the nucleotide sequence encoding the immunoglobulin Fc region comprises the sequence of which a complementary sequence is hybridized with the nucleotide sequence indicated by SEQ ID NO: 8 under stringent conditions, or comprises a degenerative variant of the nucleotide sequence indicated by SEQ ID NO: 8.

In other preferable embodiments, the FGFR-Fc fusion protein includes the FGFR-Fc fusion protein variant. In one embodiment, the variant includes the variant that contains no more than 2, 3, 4, 5 or 10 substitutions, additions or deletions of amino acid in the part derived from IFS corresponding to the amino acid sequence indicated by position 134 to position 162, position 145 to position 162, or position 151 to position 162 of SEQ ID NO: 1, and preferably, the variant retains the angiogenesis-inhibitory capacity. In another embodiment, the variant contains no more than 2, 3, 4, 5, 10 or 20 substitutions, additions and/or deletions of amino acids in the D2 domain corresponding to the amino acid sequence indicated by position 163 to position 247 of SEQ ID NO: 1, and preferably, the variant retains the angiogenesis-inhibitory capacity. In another embodiment, the variant contains no more than 2, 3, 4, 5, 10 or 20 substitutions, additions and/or deletions of amino acid in D3 domain corresponding to the amino acid sequence indicated by position 270 to position 359 of SEQ ID NO: 1, and preferably, the variant retains the angiogenesis-inhibitory capacity. In another embodiment, the substitution, addition, or deletion is located at the linker or the linking part.

In addition to the naturally occurring modifications in the part derived from the extracellular domain of FGFR and the part derived from immunoglobulin Fc region, other post-translational modifications may also be comprised in the FGFR-Fc fusion protein. Such modifications include, but are not limited to, acetylation, carboxylation, glycosylation, phosphorylation, esterification and acylation. As a result, non-amino acid components may exist in the modified FGFR-Fc fusion protein. These components may be, for example, polyethylene glycol, lipid, polysaccharide or monosaccharide, or phosphoric acid. The effect of such non-amino acid components on the function of the FGFR-Fc fusion protein may be tested as described for other FGFR-Fc fusion protein variants herein. When the FGFR-Fc fusion protein is produced in a cell, post-translational processing is also possibly important for correct folding and/or protein function. Special cell machines and unique mechanisms exist in different cells (for example CHO, HeLa, MDCK, 293, WI38, NIH-3T3 or HEK293) for these post-translational activities, and different cells may be selected by the skilled artisan to improve modification and processing of FGFR-Fc fusion protein.

The fusion protein as described herein may be produced by any method known in the art. For example, it may be produced by chemical synthesis or from nucleic acid expression. The peptides used in the present invention may be easily prepared according to the established standard liquid, or preferably, solid phase peptide synthesis method known in the art (see, for example J. M. Stewart and J. D. Young, Solid Phase Peptide Synthesis, 2" edition, Pierce Chemical Company, Rockford, Ill. (1984), in M. Bodanzsky, and A. Bodanzsky, The Practice of Peptide Synthesis, Springer Verlag, New York (1984)). The fusion protein may be produced by the techniques known in the art so that one or more intramolecular crosslinkings may be formed between the cysteine residues located in the polypeptide sequence expected to be comprised in the protein (see, for example U.S. Pat. No. 5,478,925). In addition, general modifications may be performed to the protein described herein by adding, for example, cysteine or biotin to the C-terminus or N-terminus of the protein.

As used herein, "therapeutically effective amount" or "effective amount" refers to a dosage that is sufficient to provide a benefit to the subject to whom it is administrated. The administrated dosage, the rate and the time course of administration are dependent on the condition of the patient and the severity of the disease. Finally, the physician is responsible for the prescription (for example decision on the dosage etc.) and will make a decision for the treatment, usually by considering the disease treated, individual condition of the patient, position of delivery, the method for administration and other factors known to the physician.

A series of isolated soluble FGFR-Fc fusion proteins have been constructed according to the present invention, which may bind FGF and effectively inhibit the cell division induced by FGF. The fusion protein preferably comprises: the part derived from IFS, D2, D3 and immunoglobulin Fc region.

Unexpectedly, it has also been found that the binding of FGF by the fusion protein is significantly influenced by the length of the part derived from IFS. Preferably, the part derived from IFS comprises no acidic box, and more preferably, it has the amino acid sequence corresponding to position 134 to position 162, position 145 to position 162, or position 151 to position 162 of SEQ ID NO: 1. In some preferable embodiments, the part derived from IFS comprises the fusion protein corresponding to the amino acid sequence indicated by position 145 to position 162 of SEQ ID NO: 1, which has extremely high FGF affinity and potential to effectively inhibit cell division induced by FGF.

In some embodiments of the present invention, a soluble FGFR-Fc fusion protein is provided, which comprises: D1, a part derived from IFS, D2, D3 and an immunoglobulin Fc region. Preferably, the part derived from IFS comprises no acidic box, and more preferably, it has the amino acid sequence corresponding to position 134 to position 162, position 145 to position 162, or position 151 to position 162 of SEQ ID NO: 1.

In some other embodiments of the present invention, a soluble FGFR-Fc fusion protein is provided, which comprises: a part of D1, a part derived from IFS, D2, D3 and an immunoglobulin Fc region. Preferably, the part derived from IFS comprises no acidic box, and more preferably, it has the amino acid sequence corresponding to position 134 to position 162, position 145 to position 162, or position 151 to position 162 of SEQ ID NO: 1.

In some other embodiments of the present invention, a soluble FGFR-Fc fusion protein is provided, which comprises: a part derived from IFS, D2, D3 an immunoglobulin Fc region. Preferably, the part derived from IFS comprises no acidic box, and more preferably, it has the amino acid sequence corresponding to position 134 to position 162, position 145 to position 162, or position 151 to position 162 of SEQ ID NO: 1.

In some other embodiments of the present invention, a soluble FGFR-Fc fusion protein is provided, which is sequentially composed of, from the N-terminus to the C-terminus, a part derived from IFS, D2, D3 and an immunoglobulin Fc region. Preferably, the part derived from IFS comprises no acidic box, and more preferably, it has the amino acid sequence corresponding to position 134 to position 162, position 145 to position 162, or position 151 to position 162 of SEQ ID NO: 1.

In some other embodiments of the present invention, an FGFR-Fc fusion protein is provided, which can inhibit tumor cells directly or indirectly. Preferably, the FGFR-Fc fusion protein of the present invention inhibits tumor cells directly. More preferably, the growth of tumor cells is inhibited by the FGFR-Fc fusion protein of the present invention by at least 10%, 20%, 30%, 40%, 50%, 80%, 90% or 95%. The tumor cells may be any tumor cells, for example, leukemia, lung cancer, liver cancer, head and neck cancer, stomach cancer, bladder cancer, or carcinoma of uterine or cervix etc. Preferably, the inhibition is achieved by direct binding to tumor cells.

In some embodiments, the present invention includes use of (i) a FGFR-Fc fusion protein, or (ii) a polynucleotide encoding such fusion protein, in the preparation of the compositions or medicaments for the treatment of diseases mediated by, or related to, angiogenesis. For example, in one embodiment, the present invention provides use of (i) FGFR-Fc fusion protein, or (ii) a polynucleotide encoding such fusion protein in the preparation of a medicament as an angiogenesis inhibitor.

In some embodiments, the FGFR-Fc fusion protein according to the present invention may be produced by the expression of the nucleotide sequence as indicated by any one of SEQ ID NOs: 16-22 in a mammalian cell line. The mammalian cell line can be, for example, a CHO cell line.

Additionally, in the present invention, the FGFR-Fc fusion protein as described below is provided, in which a part derived from the extracellular domain of FGFR may be fused with the immunoglobulin Fc region with or without a linker.

In some other embodiments, the present invention includes the isolated nucleic acid molecules encoding the FGFR-Fc fusion protein, and the present invention also includes use of these molecules in the manufacture of a medicament. The nucleic acid may be recombinant, synthetic or produced by any available methods in the art, and the methods include cloning by means of using standard technique.

In some other embodiments, the present invention includes a vector comprising the nucleic acid molecule of the present invention. The vector may be an expression vector, in which the nucleic acid is operatively linked to a control sequence that is able to facilitate the expression of the nucleic acid in a host cell. A plurality of vectors may be used. For example, suitable vectors may include virus (for example poxvirus, adenovirus, baculovirus etc.); or yeast vectors, bacteriophages, chromosomes, artificial chromosomes, plasmids, and cosmids.

In some embodiments, the present invention further includes the cells transfected by these vectors so that the FGFR-Fc fusion protein is expressed. The host cell suitable for the present invention may be a prokaryotic cell or eukaryotic cell. They include bacteria, for example *E. coli*; yeast; insect cells; and mammalian cells. The mammalian cell lines that may be used include, but are not limited to, Chinese Hamster Ovary (CHO) cells, baby hamster kidney cells, NS0 mouse myeloma cells, monkey and human cell lines, and derivate cell lines thereof.

In another aspect of the present invention, a method for angiogenesis inhibition is provided, comprising administering the FGFR-Fc fusion protein of the present invention to the subject in need thereof. Preferably, the method is carried out in a mammal.

In another aspect of the present invention, a method for binding FGF in vitro or in vivo is provided, which comprises contacting FGF to the fusion protein according to the present invention.

In another aspect of the present invention, a method for the treatment or prevention of tumors in a mammal is provided, which comprises administering the FGFR-Fc fusion protein of the present invention to the subject in need thereof. Preferably, the tumor is a solid tumor.

In another aspect of the present invention, a method for the treatment or prevention of ophthalmic angiogenesis-related diseases in a mammal is provided, which comprises administering the FGFR-Fc fusion protein of the present invention to the subject in need thereof. Preferably, the ophthalmic angiogenesis-related disease is age-related macular degeneration.

The present invention also relates to use of the FGFR-Fc fusion protein in the preparation of medicaments for angiogenesis inhibition. Additionally, the present invention also relates to use of the FGFR-Fc fusion protein in the preparation of medicaments for the treatment or prevention of angiogenesis-related diseases. Preferably, angiogenesis-related diseases are tumors or ophthalmic angiogenesis-related disease.

Angiogenesis-related diseases include, but are not limited to, angiogenesis-dependent cancers, including, for example, solid tumors, hematogenic tumors (for example leukemia) and tumor metastasis; benign tumors, for example, angioma, acoustic neuroma, neurofibroma, trachoma and pyogenic granuloma; rheumatoid arthritis; psoriasis; rubeosis; Osler-Webber Syndrome; myocardial angiogenesis; plaque neovascularization; telangiectasia; hemophiliac joint and angiofibroma.

In some embodiments of the methods described, one or more FGFR-Fc fusion proteins may be administrated together (simultaneously) or at a different time (sequentially).

Additionally, the fusion protein may be administered together with one or more additional medicaments used for cancer treatment or angiogenesis inhibition.

In some embodiments, the method disclosed in the present invention may be used alone. Alternatively, the subject method may be combined with other conventional anticancer therapies for the treatment or prevention of proliferative diseases (for example tumors). For example, these methods may be used for the prevention of cancers, the prevention of cancer relapse and postoperative metastasis, and may be used as a supplement for other cancer therapies. The effectiveness of conventional cancer therapies (for example, chemotherapy, radiotherapy, phototherapy, immunotherapy and operation) may be enhanced by using target polypeptide therapeutic agents.

In ophthalmology, angiogenesis is related to, for example, diabetic retinopathy, retinopathy of prematurity, age-related macular degeneration, corneal transplantation rejection, neovascular glaucoma and RLF (retrolental fibroplasia). The FGFR-Fc fusion protein disclosed herein can be administrated inside the eye or by other routes. Other diseases related to angiogenesis in ophthalmology include, but are not limited to, epidemic keratoconjunctivitis, Vitamin A deficiency, contact lens overwear, atopic keratitis, superior limbic keratitis, pterygium keratitis sicca, sjogren, acne rosacea, phlyctenosis, syphilis, Mycobacteria infection, lipid degeneration, chemical burn, bacterial ulcer, fungal ulcer, Herpes simplex infection, Herpes zoster infection, protozoan infection, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy and corneal graph rejection, sickle cell anemia, sarcoid, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infection resulting in retinitis or choroiditis, presumed ocular histoplasmosis, Bests disease, myopia, optic pit, Stargarts disease, pars planitis, chronic retinal detachment, hyperviscosity syndromes, toxoplasmosis, trauma and post-laser complication. Other diseases include, but not limited to, rubeosis (neovasculariation of the angle) related diseases and diseases induced by abnormal hyperplasia of the fibrous blood vessel or fibrous tissue, including all kinds of proliferative vitreoretinopathy.

Administration

The fusion protein of the present invention may be administrated alone, but preferably, as a pharmaceutical composition, which usually comprises a suitable pharmaceutical excipient, diluent or carrier selected according to the intended administration route. The fusion protein may be administrated to the patient in need thereof by any suitable route. A precise dosage will be dependent on many factors, including exact properties of the fusion protein.

Some suitable administration routes include (but are not limited to) oral, rectal, nasal, topical (including buccal and sublingual), subcutaneous, vaginal or parenteral (including subcutaneous, intramuscular, intravenous, intracutaneous, intrathecal and extradural) administration.

For intravenous injection and injection at the focal site, active ingredients are present in the form of a parenterally-acceptable aqueous solution, which is free of pyrogen and has appropriate pH value, isotonicity and stability.

A suitable solution may be well formulated by the skilled one in the art using, for example, isotonic excipients such as sodium chloride injection, Ringer's injection, Ringer's lactate injection. As required, preservative, stabilizer, buffering agent, antioxidant and/or some other additives may be added. The pharmaceutical composition orally administrated may be in a form of tablet, capsule, powder or oral liquid etc. Solid carrier, such as gelatin or adjuvant, may be comprised in a tablet. Liquid pharmaceutical composition usually comprises liquid carrier, such as water, petroleum, animal or vegetable oil, mineral oil or synthetic oil. Also included may be normal saline solution, glucose or other sugar solutions or glycols such as ethylene glycol, propylene glycol or polyethylene glycol.

Examples of the techniques and schemes as mentioned above and other techniques and schemes as used according to the present invention may be found in Remington's Pharmaceutical Sciences, 16th edition, Oslo, A. (ed), 1980.

Cloning of the Fusion Protein and Construction of the Expression Plasmid

The FGF receptor fragment can be obtained from the amplification of a cDNA template of a corresponding receptor through PCR. The IgG1 Fc fragment can be obtained from the cDNA amplification of the human-derived IgG1 through PCR. When PCR primers are designed, linking sequences are introduced between different fragments so that these different fragments may be finally linked by overlap PCR to form reading frames for different fusion proteins, and endonuclease BspE I and Pst I sites can be added to both ends of the cDNA. The cDNAs for different fusion proteins may be cloned to the expression plasmid after digestion by BspE I and Pst I. The plasmid after cloning may be determined by endonuclease digestion, electrophoresis and finally DNA sequencing.

Expression and Purification of the Fusion Protein

The present fusion protein may be expressed and purified by techniques commonly used in the art. DNA from corresponding fusion protein plasmid was purified using plasmid purification kit (MAX) available from Qiagen, and the concentration of plasmid DNA can be determined using UV spectrophotometry, and the plasmid was transfected to CHO cell using FUGENE 6 liposome (Roche). Specific methods for transfection can be performed according to the specification of the product.

Based on the expression amount required for the proteins, two methods were employed in the present invention for protein expression: (1) transient expression, in which the fusion protein contained culture supernatant was usually harvested 48-72 h after transfection, and the relative content of the fusion protein was then determined using human IgG ELISA so that the fusion protein may be rapidly and efficiently obtained; (2) establishing a stable cell line and producing the common DHFR-defective CHO cell expression system using the recombinant protein medicament expression, the basic process of which includes cell transfection, selection of stably transfected cell, clone screening, stress amplification, culture medium and process optimization etc., and finally realizing a large-scale suspension culture of CHO engineering cell strain in a serum free culture medium. The culture product was collected and the fusion protein was purified using Protein A affinity column. The purified protein was analyzed by sodium dodecyl sulfate polyacrylamide gel electrophoresis (SDS-PAGE), and subsequently all eluates in which the required expression product was contained were combined and filtered using a 0.22 μm filter, and then protein quantification was carried out according to a plurality of methods such as Lowry protein assay. The volume of CHO cell culture in the present invention was at a level of 10 L bioreactor, through which the fusion protein obtained after purification could satisfy the protein amount required in the animal experiments, and also a basis was established for future scaling-up.

Neutralization of FGF by the Fusion Protein was Validated at a Level of Protein

After the fusion protein expressed by CHO was obtained, the binding capacity of the fusion protein to FGF is evaluated in the present invention at a level of protein. Binding experiment and affinity experiment were performed for validation in the present invention, in which steps of the binding experiment included: after initially coated by FGF-2 on a 96-well ELISA plate, the coated well was blocked by BSA followed by adding each fusion protein at the same concentration, and then a secondary antibody to human IgG Fc-HRP was added after washing, and the samples were developed, stopped and read at 450 nm on a ELISA plate, and finally the fusion protein which had binding capacity to FGF-2 was screened based on the signal strength. The affinity experiment was performed in order to determine the affinity of the fusion protein to FGF-2 in the solution system, which comprised the following steps: FGF-2 was initially coated on a 96-well ELISA plate to capture the antibody, and then the coated well was blocked by BSA, and subsequently a mixture of the fusion protein and FGF-2 which was previously prepared and incubated were added with a gradient of diluted standards, and after incubation, an HRP-labeled detection antibody was added (using antibody 2 which specifically detected free VEGF or FGF-2), and subsequently the samples were developed, stopped and read at 450 nm on a ELISA plate, and finally the relative concentration of free FGF-2 was detected in the mixture of the fusion protein and FGF-2. Through the experiments above, the fusion protein having a blocking effect on FGF-2 was screened.

Neutralization of FGF by the Fusion Protein was Validated at a Cellular Level

After the binding capacity of the fusion protein to FGF-2 was determined at a level of protein, its angiogenesis-inhibiting effect will be further validated at a cellular level in the present invention. The inhibition capacity of the fusion protein on the division and migration of the vascular endotheliocyte is examined by the division test using human umbilical vein endothelial cell (HUVEC) and the HUEVC cell migration test. The inhibition capacity of the fusion protein on the division of HUVEC cell can be examined by the HUVEC cell division test, which comprises the following steps during the experiment: 3000 HUVEC cells/well were inoculated to a 96-well plate and cultured at 37° C. in an incubator supplemented with 5% $CO_2$, and then FGF-2 as well as a mixture of the fusion protein at different concentrations with FGF-2 are added respectively, and after culturing for another 3-4 days, 10% CCK-8 is added and cultured for 2 h before the sample is read at 450 nm on a ELISA plate. The inhibition capacity of the fusion protein on the division of vascular endotheliocyte induced by FGF-2 was evaluated based on the difference of absorbance, and the median effective concentration of the fusion protein was obtained for FGF-2 inhibition. The inhibition capacity of the fusion protein on HUVEC cell migration was examined by the HUVEC cell migration test, which comprises the following steps during the experiment: 50000 HUVEC cells as well as the fusion protein at various concentrations were initially inoculated in the upper chamber, while 600 μL FGF-2 containing culture liquid was added into the lower chamber, and subsequently, the sample was cultured at 37° C. in an incubator supplemented with 5% $CO_2$ for 20-24 h before cells on the face side of the membrane of the upper chamber were removed, and then cells on the back side of the membrane were fixed, stained and washed with PBS before observed and counted under an inverted microscope. The migration of HUVEC cells induced by the stimulation of FGF-2 was demonstrated by counting the HUVEC cells on the back side of the membrane, and the inhibition capacity of the fusion protein on the migration of the vascular endotheliocyte was tested by adding the fusion protein at various concentrations into the culture liquid. Through the experiments mentioned above, the inhibition capacity of the new fusion protein constructed in the present invention was validated on the division and migration of the vascular endotheliocyte induced by FGF-2, which also provided a basis for future animal experiments.

Tumor Growth-Inhibiting Capacity of the Fusion Protein was Validated by the Tumor Model After the blocking effect of the new fusion protein in the present invention on FGF-2 signal was demonstrated by experiments at a protein level and a cellular level, its anti-tumor capacity would be tested in animal tumor models in the present invention. In the present invention, the anti-angiogenesis and anti-tumor effect of the fusion protein would be validated by models commonly used in searching medicaments for angiogenesis and tumor, for example, LLC mouse lung cancer, U87 gliocytoma, B 16 melanoma and so on. In animal experiments, in addition to conventional control groups, control medicaments, such as VEGF-Trap, FP-1039, would also be included so as to obtain comparative data for anti-tumor capacity. During experiments, 100 μL tumor cell liquid with appropriate amount was subcutaneously injected into C57 mouse on one side of the back, and the tumor volume was measured with a vernier caliper twice a week. Upon the tumor grew to about 200 $mm^3$, the fusion protein at various concentrations was subcutaneously injected and the mice were sacrificed after 2-3 weeks. Subsequently, the tumor volume was measured with a vernier caliper, and the anti-tumor effect of the fusion protein was validated by the size of the tumor. Furthermore, individual tumor tissue was analyzed using methods such as immunohistochemistry to investigate the regulation mechanism of angiogenesis.

EXAMPLES

Example 1

Construction of Recombinant Expression Plasmid for FGFR1-Fc Fusion Protein

The FGF receptor fragment is obtained from the amplification of the cDNA templet of FGF receptor through PCR, and IgG1 Fc fragment is obtained from the cDNA amplification of the human-derived IgG1 through PCR. A commercially available cDNA (PCR Ready First Strand cDNA, derived from human adult colon cancer tissue, BioChain) was used as the template for FGFR1 fragment. Total RNA was extracted from the blood of healthy human subjects using human blood RNA extraction kit (QIAGEN). According to the manufacturer's instruction of reverse transcription kit (Promega), RT-PCR was performed using M-MLV reverse transcriptase (Promega) so that RNA was reversely transcripted to cDNA which was used as the template for IgG1 Fc fragment. RT-PCR was performed according to the manufacturer's instruction of reverse transcription kit, which has the following steps: Oligo dT, dNTP, total RNA and DEPC H2O were mixed homogeneously and reacted at 70° C. for 10 min before placed on ice for 5 min, and subsequently RNase inhibitor, M-MLV reverse transcriptase and reaction buffer were added. The mixture was reacted at 42° C. for 1 h and subsequently at 70° C. for 15 min, and the cDNA obtained may be used as the template.

Various FGFR1 fragments were individually amplified by PCR using the cDNA from human adult colon cancer tissue as the template (the primers were listed in table 1), and IgG1 Fc fragment was amplified by PCR using human blood cDNA as the template (the primers were listed in table 1 and 2). The reaction conditions for the PCR were as follows: 5 min of pre-denaturalization at 98° C., total 30 cycles of 30 s of denaturalization at 98° C., 45 s of annealing at 56° C. and 2 min of extension at 72° C., and finally another 10 min of extension. When PCR primers were designed, 20 or more complementary base sequences were introduced as the linking sequence between FGFR1 fragment and IgG1 Fc fragment so that the FGFR1 fragment and IgG1 Fc fragment may be subsequently linked by overlap PCR to form reading frames for different fusion proteins, and at the same time, restriction endonuclease BspE I and Pst I site were added at both ends of the PCR product.

Subsequently, overlap PCR was carried out to obtain each FGFR1-Fc fusion protein fragment by amplification. The process of the overlap PCR reaction may be divided into two rounds, in which the fragment required for linking and containing no primer was included in the first round with reaction conditions as follows: 5 min of pre-denaturalization at 98° C., 6 cycles of 30 s of denaturalization at 98° C., 45 s of annealing at 56° C. and 5 min of extension at 72° C., and finally another 10 min of extension at 72° C.; after the first round, the second round of PCR was carried out by adding the primers for both ends with reaction conditions as follows: 5 min of pre-denaturalization at 98° C., 30 cycles of 30 s of denaturalization at 98° C., 45 s of annealing at 56° C. and 2 min of extension at 72° C., and finally another 10 min of extension at 72° C.; through the process above, reading frames for different fusion proteins were spliced, and at the same time, restriction endonuclease BspE I and Pst I site were added at both ends of the cDNA.

After amplification, the fragments amplified by PCR were purified using QIAquick PCR purification kit (QIAGEN). cDNAs of various fusion proteins and the eucaryotic expression plasmid pSV2-dhfr (ATCC) were digested by BspE I and Pst I, respectively. Subsequently, 1% agarose gel electrophoresis was performed on the digested samples under a voltage of 90 V. Target fragments were recovered using QIAquick gel extraction kit (QIAGEN) before ligating at 16° C. for 1 h using a ligase (NEB). The mixture for ligation reaction was transformed to the competent Top10 *E. coli* under the conditions of 90 s of reaction at 42° C. followed by 3 min of standing on ice. After the sterile LB culture broth (free of antibody) added, the mixture was shaken at 250 rpm in a shaker at 37° C. for 1 h before coating on a LB plate supplemented with ampicillin. The plate was cultured overnight in a thermostated incubator at 37° C., and then single colonies were picked out and transferred to an ampicillin-containing LB culture broth. The inoculated culture broth was shaken at 250 rpm in a shaker at 37° C. overnight before the plasmid was extracted using alkaline lysis. Subsequently, the sample was digested by restriction endonuclease before evaluated by 1% agarose gel electrophoresis under a voltage of 90 V. The recombinant plasmid with correct endonuclease digestion was confirmed by DNA sequencing. Based on the steps above, 19#, 13#, 22#, 23#, 26#, 29# and 8# expression plasmid for FGFR1-Fc fusion protein were constructed. The protein sequence of FGFR1-Fc in each fusion protein and its encoding nucleotide sequence were listed in Table 3. The schematic diagram of the fusion protein structure was shown in FIG. 1.

TABLE 1

Primers used for amplification of FGFR1 fragment

| Fusion protein | Upstream primer | Downstream primer |
|---|---|---|
| 19# | 19#-FGFR1For (SEQ ID NO: 24) TAGTTCCGGAAGGCCGTCCCCGACCTTGCCTG | FGFR1Rev (SEQ ID NO: 31) GTTTTGTCCTCCAGGTAC AGGGGCGAGGTC |
| 13# | 13#-FGFR1For (SEQ ID NO: 25) TAGTTCCGGAAAAAATCGCACCCGCATCACAG | FGFR1Rev |
| 22# | 22#-FGFR1For (SEQ ID NO: 26) TAGTTCCGGAGTAACCAGCAGCCCCTCGGGC | FGFR1Rev |
| 23# | 23#-FGFR1For (SEQ ID NO: 27) TAGTTCCGGATCCTCTTCAGAGGAGAAAGAAAC | FGFR1Rev |
| 26# | 26#-FGFR1For (SEQ ID NO: 28) TAGTTCCGGAAAACCTAACCCCGTAGCTCCAT | FGFR1Rev |
| 29# | 29#-FGFR1For (SEQ ID NO: 29) TAGTTCCGGACCATATTGGACATCCCCAGAAAAG | FGFR1Rev |
| 8# | 8#-FGFR1For (SEQ ID NO: 30) CTAGCTCCGGACCAGAAAAGATGGAAAAGAAATTGC | FGFR1Rev |

TABLE 2

Primers used for amplification of IgG1 Fc fragment

| | Upstream primer | Downstream primer |
|---|---|---|
| IgG1 Fc fragment | FcFor (SEQ ID NO: 32) CTGTACCTGGAGGACAAAACT CACACATGC | FcRev (SEQ ID NO: 33) GATATCTGCAGTCATTT ACCCGGAGACAGG |

TABLE 3

Protein sequences and nucleotide sequences for FGFR1-Fc fusion proteins

| Fusion protein | Protein Sequence | Nucleotide Sequence |
|---|---|---|
| 19# | SEQ ID NO: 9 | SEQ ID NO: 16 |
| 13# | SEQ ID NO: 10 | SEQ ID NO: 17 |
| 22# | SEQ ID NO: 11 | SEQ ID NO: 18 |
| 23# | SEQ ID NO: 12 | SEQ ID NO: 19 |
| 26# | SEQ ID NO: 13 | SEQ ID NO: 20 |
| 29# | SEQ ID NO: 14 | SEQ ID NO: 21 |
| 8# | SEQ ID NO: 15 | SEQ ID NO: 22 |

Example 2

Transient Expression and Quantification of the Fusion Proteins

The DNA of individual fusion protein plasmid was purified using MAX Plasmid Purification Kit (Qiagen). The concentration of the plasmid DNA was determined by UV spectrophotometry. 1 µg recombinant plasmid and 6 µL liposome (FuGENE 6 Transfection Reagent, Roche) were homogeneously mixed into 100 µL fresh IMDM culture broth (GIBCO); after standing for 15 min, the mixture was added to the CHO cells (ATCC) cultured overnight after inoculation at a cell density of $3 \times 10^5$/mL into a 6-well plate; the mixture was cultured at 37° C. in an incubator supplemented with 5% $CO_2$ for 48 h with a cell complete culture broth (IMDM medium containing 10% FBS, 1% HT and 1% glutamine, all supplied by GIBCO); subsequently, the supernatant was collected and determined for the relative content of the fusion protein using human IgG ELISA kit for protein quantification (BETHYL). The relative content of the fusion protein expressed and secreted by CHO was determined with the following steps: 100 µL anti-human IgG-Fc protein (10 µg/mL) purified by affinity was coated to a 96-well ELISA plate (IMMULON) and subsequently washed for 5 times using 300 µL PBST washing solution; each coated well was blocked with 200 µL freshly prepared blocking working solution (blocking stock solution:PBS=1:19) and incubated at 37° C. for 1 h; after washed in 300 µL PBST washing solution for 5 times, 100 µL IgG solution diluted in a gradient (200 ng/mL original concentration and diluted by PBS in the multiple proportion of 1:2) as a standard and 100 µL culture supernatant of each fusion protein diluted in a gradient (starting with the concentration of each culture supernatant, and diluted by PBS in the multiple proportion of 1:5) were added to each well and incubated at 37° C. for 2 h; after washed in 300 µL PBST washing solution for 5 times, 100 µL anti-human IgG Fc-HRP secondary antibodies diluted with PBS in a ratio of 1:10000 was added and incubated at 37° C. for 1 h; after washed, the well was developed by adding 100 µL developing solution (KPL); finally, after the development was stopped by adding 100 µL stopping solution (KPL), the absorbance of the ELISA plate was read at a wavelength of 450 nm on a ELISA reader. The concentrations of various fusion proteins may thereby be determined according to the standard curve.

Example 3

Binding of the Fusion Proteins

The binding capacity of 19#, 13#, 22#, 23#, 26#, 29# and 8# fusion protein constructed above to FGF-2 was detected by ELISA.

Initially, a 96-well ELISA plate (IMMULON Company) was coated by 100 µL solution containing 50 ng/mL FGF-2 (R&D Systems) as well as containing 100 ng/mL heparin (Sigma Company) and 50 ng/mL FGF-2. Subsequently, the plate was washed by 300 µL PBST washing solution for 5 times before each coated well was blocked by 200 µL freshly prepared blocking working solution (KPL Company) (blocking stock solution:PBS=1:19) and incubated at 37° C. for 1 h. After washed in 300 µL PBST washing solution for 5 times, 100 µL solutions of various fusion proteins (dissolve in PBS, pH=7.2, concentration of 20 ng/ml) were added and incubated at 37° C. for 2 h. After washed in 300 µL PBST washing solution for 5 times, 100 µL secondary antibody to human IgG Fc-HRP (BETHYL Company) diluted with PBS in a ratio of 1:10000 was added and incubated at 37° C. for 1 h. After washing in 300 µL PBST washing solution 5 times, the well was developed to the presence of color at room temperature in a dark place by adding 100 µL developing solution (KPL Company), and finally the development was stopped by adding 100 µL stopping solution (KPL Company) before the absorbance of the ELISA plate was read at a wavelength of 450 nm on a ELISA reader.

The higher the binding capacity of the fusion protein to FGF2, the larger the absorbance and the stronger the signal. Based on the strength of the signal, 26# fusion protein was determined to have the highest binding capacity to FGF-2.

Figure 2:
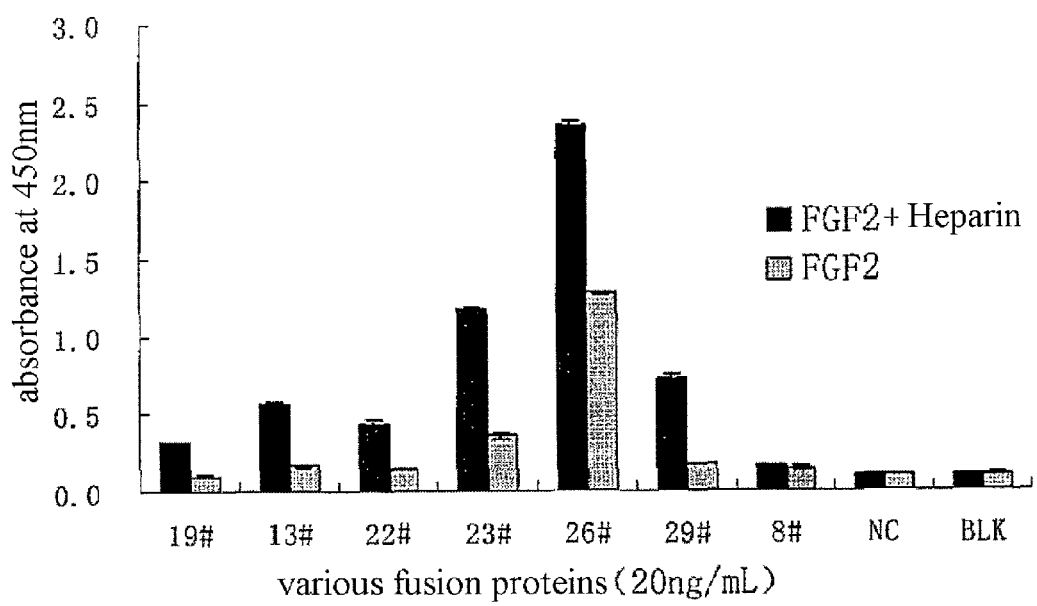
FIG. 2 shows a comparison of FGF-2 binding among various FGFR1-Fc fusion proteins. Binding of heparin (100 ng/mL) containing FGF-2 (50 ng/mL) or FGF-2 (50 ng/mL) alone to each FGFR1-Fc fusion protein (20 ng/mL) is detected by ELISA.

Comparison of FGF-2 binding among various fusion proteins is shown in FIG. 2. It can be seen from FIG. 2 that 19#, 13#, 22#, 23#, 26# and 29# fusion protein bound to FGF at different extents in the presence of heparin, and particularly, the binding extent of 23#, 26# and 29# was extremely higher than control, and higher than that of 19#, 13# and 22#, indicating that the fusion proteins containing no acidic box had excellent effect.

Among others, especially high binding extent was demonstrated by 26#, indicating that the fusion protein had significantly better binding effect when it comprises a part of certain length derived from the intermediate functional sequence of the Ig-like domain of FGFR.

Example 4

Stable Expression and Purification of the Fusion Proteins

DHFR-defective CHO cells (ATCC) were transfected by the recombinant expression plasmid of 26# fusion protein (possessing a high FGF-2 binding capacity) through a liposome (Roche).

Particularly, 5 µg recombinant plasmid and 30 µL liposome (FuGENE 6 Transfection Reagent, Roche) were homogeneously mixed into 100 µL fresh IMDM culture broth (GIBCO); after standing for 15 min, the mixture was added to the DHFR-defective CHO cells (ATCC) cultured overnight after inoculation at a cell density of $3 \times 10^5$/mL in a 10 cm culture dish (Corning); the mixture was cultured at 37° C. in an incubator supplemented with 5% $CO_2$ for 2-3 days with a cell complete culture broth containing 10% FBS, 1% HT and 1% glutamine in a IMDM culture medium (all supplied by GIBCO); subsequently, the cells were digested by trypsin (GIBCO), inoculated at a cell density of $3 \times 10^5$/mL in 30 mL serum-free 302 culture medium (SAFC) in a flask, and selectively cultured at 37° C. in an incubator supplemented with 5% $CO_2$ at 100 rpm to a cell density of $10^6$/mL.

Subsequently, 3000 cells were inoculated into a 10 cm culture dish (Corning) (the culture broth containing 10% FBS and 1% glutamine in an IMDM culture medium) and cultured at 37° C. in an incubator supplemented with 5% $CO_2$ to form single clones.

Figure 3:
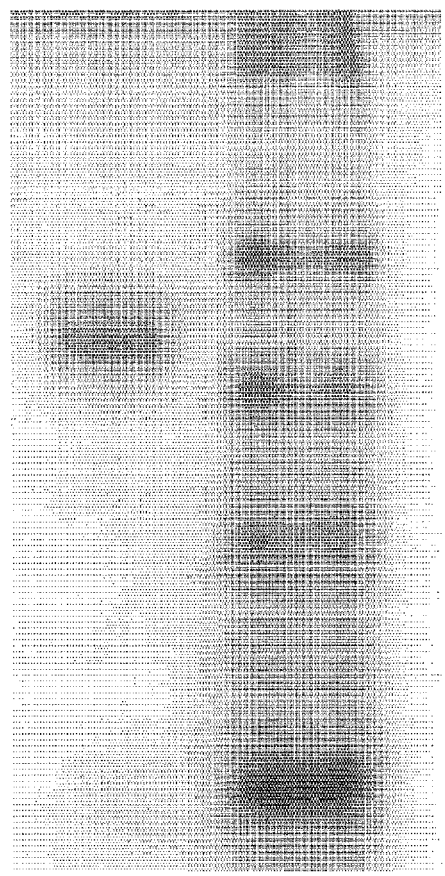
FIG. 3 shows SDS-PAGE of 26# FGFR1-Fc fusion protein.

These single clones were picked out and cultured in a 96-well plate (Corning). The relative content of the fusion protein expressed and secreted by each individual single clone was determined using a human IgG ELISA kit for protein quantification (BETHYL) under the same conditions and steps as described in Example 2 for the determination of the relative content of the fusion protein. The clone with the highest expression amount was screened out and transferred to a 6-well plate for culturing to a confluence rate of about 70%. The cells were digested by trypsin and transferred to a 10 cm culture dish. Subsequently, gradual stress amplification was carried out by adding methotrexate (MTX, Sigma) with various concentrations (10 nM, 20 nM, 50 nM, 100 nM, 200 nM and 500 nM). After stress amplification, the cells were digested by trypsin and inoculated at a cell density of $3\times10^5$/mL in a flask. The expression amount of a single cell was determined so that genetically engineered stains of CHO were obtained for expressing a particular fusion protein. Finally, large-scale suspension culture (volume of 10 L) of the genetically engineered stain of CHO was carried out at 37° C., 5% $CO_2$, 40% dissolved oxygen and 80 rpm in a serum-free 302 culture medium (pH 7.0, SAFC). The culture product was collected by centrifugation. After the supernatant was filtered using 0.45 μm filter membrane (Millipore), affinity chromatography was performed according to the instruction manual of Protein A affinity column (GE) with the specific steps as follows: initially, a protein A affinity column was equilibrated by a PBS buffer (pH 7.0); subsequently, the supernatant was loaded on the column and washed again with the PBS buffer; finally, the column was eluted with a citric acid buffer (pH 3.0), and the eluent was collected and filtered by a 0.45 μm filter membrane. After virus inactivation by adding S/D (0.3% tributyl phosphate/1% Tween 80) at 24° C. for 6 h, the target protein was further purified by a molecular sieve chromatography with the following steps: first, the eluent obtained from the Protein A affinity chromatography was dialyzed in a dialysis bag against a PBS buffer; subsequently, the sample was concentrated in a 10 KD ultrafiltration cup (Millipore); the sample concentrated using the ultrafiltration cup was then loaded on a molecular sieve chromatography column Superdex 200 (GE) equilibrated by a PBS buffer, and subsequently the column was eluted with a PBS buffer and the eluting peak was collected. The purified protein was analyzed by SDS-PAGE (FIG. 3); and subsequently, the eluates containing the required expression product was combined and filtered with a 0.22 μm filter membrane (Millipore) before the protein content was determined using many methods such Lowry protein assay.

Example 5

Gradient-Binding Experiment of the Fusion Proteins

The binding capacities of the fusion proteins as constructed above to FGF-2 were detected by ELISA, similarly as in Example 3.

Figure 4:
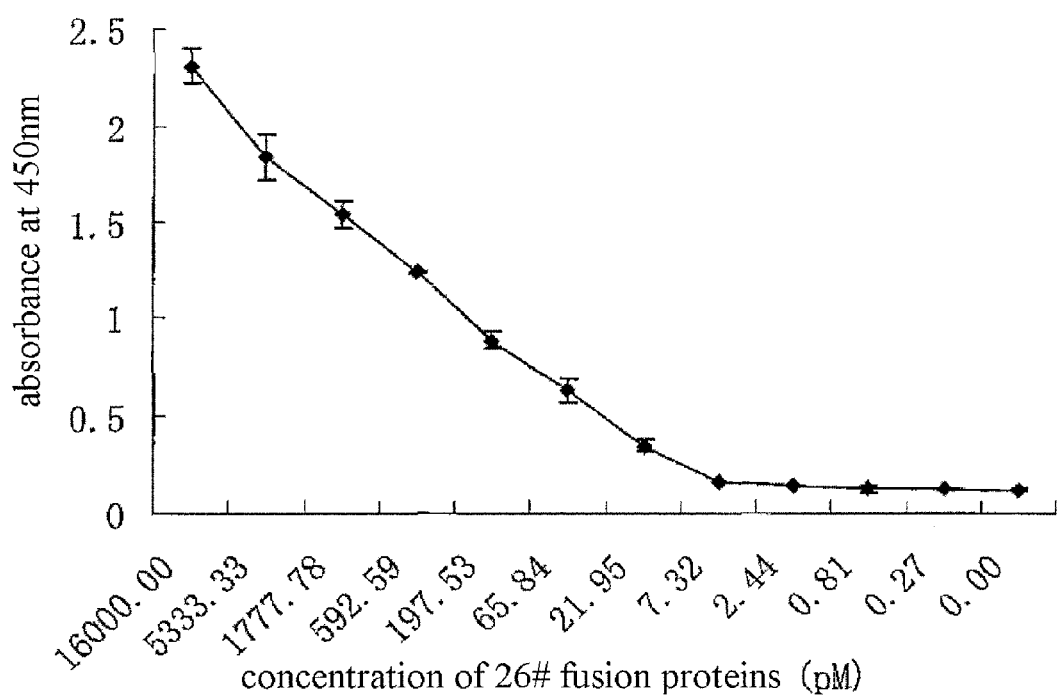
FIG. 4 shows the binding of FGF-2 to a gradient concentration of 26# FGFR1-Fc fusion protein.

Initially, a 96-well ELISA plate was coated by 100 μL solution containing 50 ng/mL FGF-2 (R&D Systems). Subsequently, the plate was washed in 300 μL PBST washing solution for 5 times before each coated well was blocked by 200 μL freshly prepared blocking working solution (KPL) (blocking stock solution:PBS=1:19) and incubated at 37° C. for 1 h. After washed in 300 μL PBST washing solution for 5 times, 100 μL solutions containing various fusion proteins at different concentrations (the starting content of protein was 16000 pM, and was diluted in a ratio of 1:3) were added and incubated at 37° C. for 2 h. After washed in 300 PBST washing solution for 5 times, 100 μL anti-human IgG Fc-HRP secondary antibody (BETHYL) diluted with PBS in a ratio of 1:10000 was added and incubated at 37° C. for 1 h. After washed in 300 μL PBST washing solution for 5 times, the well was developed by adding 100 μL developing solution (KPL), and finally the development was stopped by adding 100 μL stopping solution (KPL) before the absorbance of the ELISA plate was read at a wavelength of 450 nm on a ELISA reader. Based on the intensity of the signal, the gradient binding capacities of the fusion proteins to FGF-2 were determined. In the experiment procedure mentioned above, specific conditions and steps may be found in Example 3. Gradient binding of 26# fusion protein to FGF-2 was compared in FIG. 4. It can be seen that the binding capacity of 26# fusion protein to FGF-2 was dose-dependent.

It has been suggested by this example that the binding capacity to FGF-2 increased with an enhanced molar concentration of 26# fusion protein, manifested by a stronger signal at a wavelength of 450 nm; while the binding capacity to FGF-2 decreased correspondingly with a gradient dilution of the molar concentration of 26# fusion protein.

Example 6

Affinity Experiment of the Fusion Proteins

The affinity of the fusion protein to FGF-2 in a solution system was deter mined by an affinity experiment.

Figure 5:
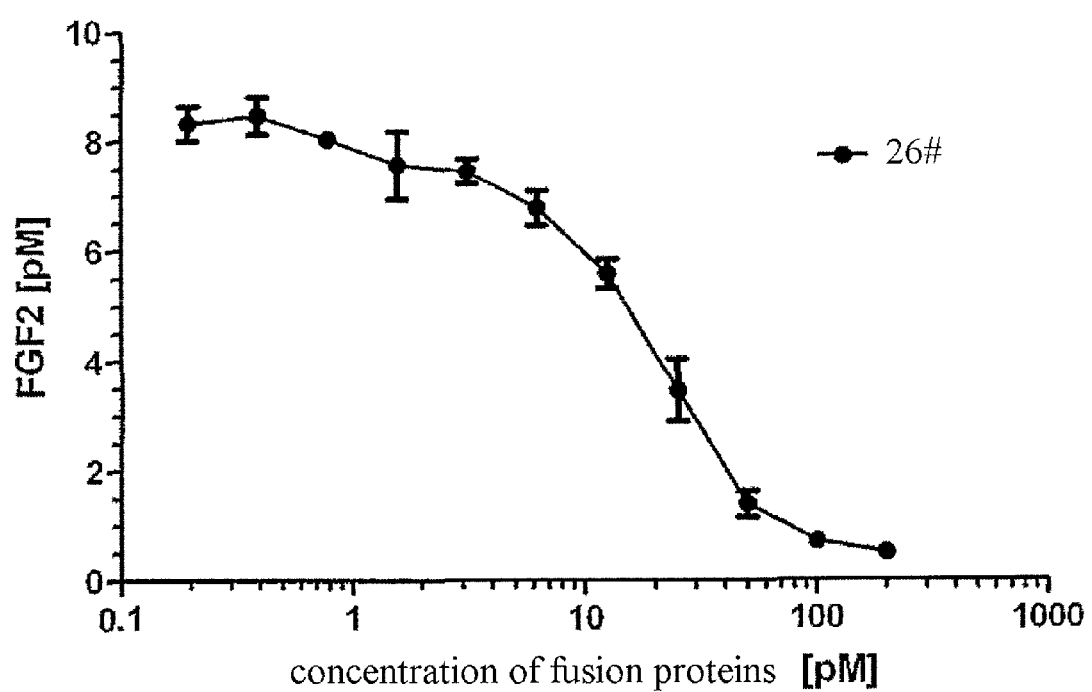
FIG. 5 shows the affinity between 26# FGFR1-Fc fusion protein and FGF-2.

Initially, a 96-well ELISA plate was coated by 100 μL solution containing 2.0 μg/mL FGF-2 capture antibody (R&D Systems). Subsequently, the plate was washed in 300 μL PBST washing solution for 5 times before each coated well was blocked by a blocking working solution (KPL) (as seen in Example 3) and incubated at 37° C. for 1 h. After washed in 300 μL PBST washing solution for 5 times, previously prepared and incubated (4° C. overnight) mixture of the fusion proteins and FGF-2 as well as the standard (R&D Systems) diluted in a gradient were added, in which the specific preparation procedure was as follows: the starting concentration of 26# fusion protein was 400 pM (dissolved in PBS) and diluted in a gradient ratio of 2-fold, and the solutions of the fusion protein were 1:1 mixed with 20 pM FGF-2 solution (dissolved in PBS), and that is, the starting final concentration of each fusion protein was 200 pM, and the final concentration of FGF-2 was 10 pM in the mixture solution prepared. The plate was incubated at 37° C. for 2 h and washed in 300 μL PBST washing solution for 5 times before 100 μL FGF-2 detection antibody solution (250 ng/mL) was added (R&D systems, which may specifically detect free antibodies against FGF-2). The plate was incubated at 37° C. for 2 h and washed in 300 μL PBST washing solution for 5 times, and subsequently, HRP labeled streptavidin (R&D systems) was added (diluted by PBS in 1:200). The plate was incubated at 37° C. for 2 h and washed in 300 μL PBST washing solution for 5 times before the well was developed at room temperature in a dark place for an appropriate duration (about 15-30 min) by adding 100 μL developing solution (KPL). Finally, after the development was stopped by adding 100 μL stopping solution (KPL), the absorbance of the ELISA plate was read at a wavelength of 450 nm on a ELISA reader. The relative concentration of free FGF-2 in the mixture of the fusion protein and FGF-2 was determined. The affinity between 26# fusion protein and FGF-2 in a solution system can be seen in FIG. 5. As demonstrated in this Example, 26# fusion protein had high affinity to FGF-2 in a solution system. The affinity increased with an enhanced concentration, which is manifested as a decreased amount of free FGF-2 with an enhanced concentration of the fusion protein. The affinity between 26# fusion protein and FGF-2 in a solution system can be seen in FIG. 5. As demonstrated in this Example, 26# fusion protein had affinity to FGF-2 in a solution system. The affinity increased with an enhanced concentration, which is manifested as a decreased amount of free FGF-2.

Example 7

Inhibitory Test for Division on Human Umbilical Vein Endothelial Cell

The inhibitory ability of the fusion proteins on the division of vascular endothelial cells was examined in a division test for human umbilical vein endothelial cell (HUVEC).

HUVEC cells (AllCells) were cultured to the exponential growth phase in an HUVEC complete medium (AllCells) at 37° C. in an incubator supplemented with 5% $CO_2$. HUVEC cells were counted after digested by trypsin. 3000 HUVEC cells were inoculated per well in an HUVEC basal medium containing 1% FBS (AllCells) in a 96-well plate. The plate was cultured overnight at 37° C. in an incubator supplemented with 5% $CO_2$.

Figure 6:
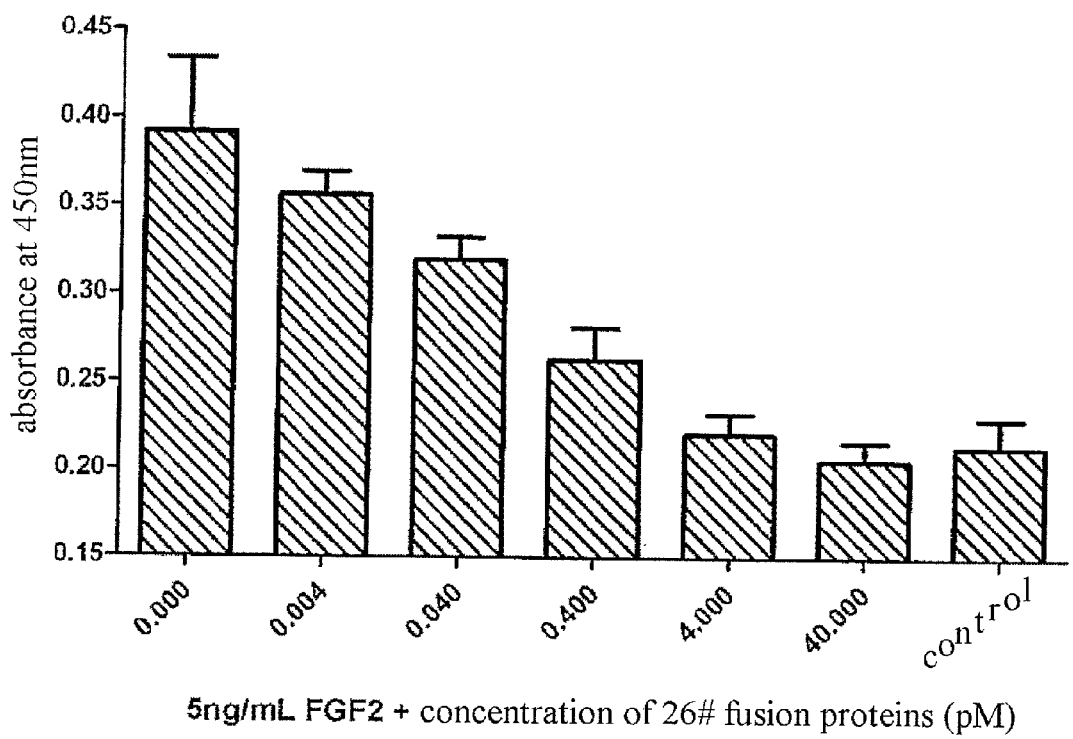
FIG. 6 shows the effect of 26# FGFR1-Fc fusion protein on the HUVEC cell division induced by FGF-2.

100 μL FGF-2 (R&D Systems) solution (final concentration of 5 ng/mL) diluted by an HUVEC basal medium containing 1% FBS, as well as 100 μL mixture of various amount of 26# fusion protein and FGF-2 (in which the final concentration of the fusion protein was 40 pM, diluted in an HUVEC basal medium containing 1% FBS with a ratio of 1:10, and the final concentration of FGF-2 was 5 ng/mL) were added and cultured for another 3-4 days. Subsequently, the culture medium was taken out and a culture medium containing 10% CCK-8 (DOJINDO) was added for another 2 h of culture before the absorbance of the 96-well plate was read directly at a wavelength of 450 nm on an ELISA reader. Based on the difference of the absorbance, the inhibitory ability of the fusion protein on the division of vascular endothelial cells induced by FGF-2 was determined. The effect of the fusion protein on HUVEC cell division induced by FGF-2 was shown in FIG. 6. As demonstrated in this Example, 26# fusion protein has biological activity and function at the cellular level, which can inhibit HUVEC cell division induced by FGF-2, and has the binding capacity to FGF-2. Such binding capacity increases as the molar concentration of 26# fusion protein increases, which is indicated by the inhibition of HUVEC cell division induced by FGF-2.

Example 8

Anti-Tumor Efficacy of FGFR-Fc in Renal Carcinoma Model

Figure 7:
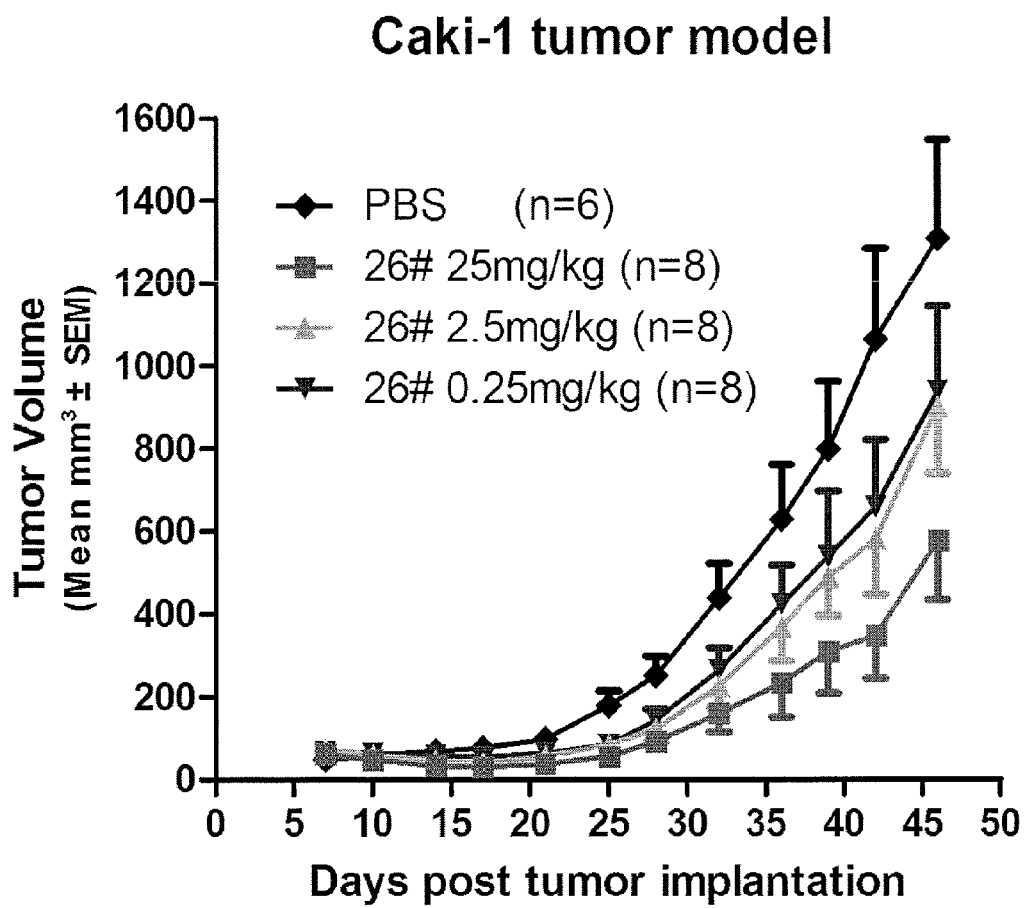
FIG. 7 shows the anti-tumor efficacy of FGFR-Fc in renal carcinoma model

Human renal carcinoma cell line Caki-1 cells ($2 \times 10^6$ cells/mouse) and human lung carcinoma cell line A549 cells ($5 \times 10^6$ cells/mouse) were suspended in serum-free medium and s.c. injected into the right flanks of 6 to 8 weeks old female, athymic BALB/c nu/nu mice. Tumor volume was calculated twice a week with a caliper by the formula of [(length×width×width)/2]. When tumor size reached around 50~100 $mm^3$, animals were randomized into four groups and received a s.c. injection of FGFR-Fc (#26 fusion protein) at a dose of 25, 2.5, 0.25 mg/kg and PBS twice weekly for 6 to 8 weeks. 3 days after the last dose, animals were sacrificed and tumors were measured. The results are shown in FIG. 7.

Example 9

Anti-Tumor Efficacy of FGFR-Fc in Lung Carcinoma Model

Figure 8:
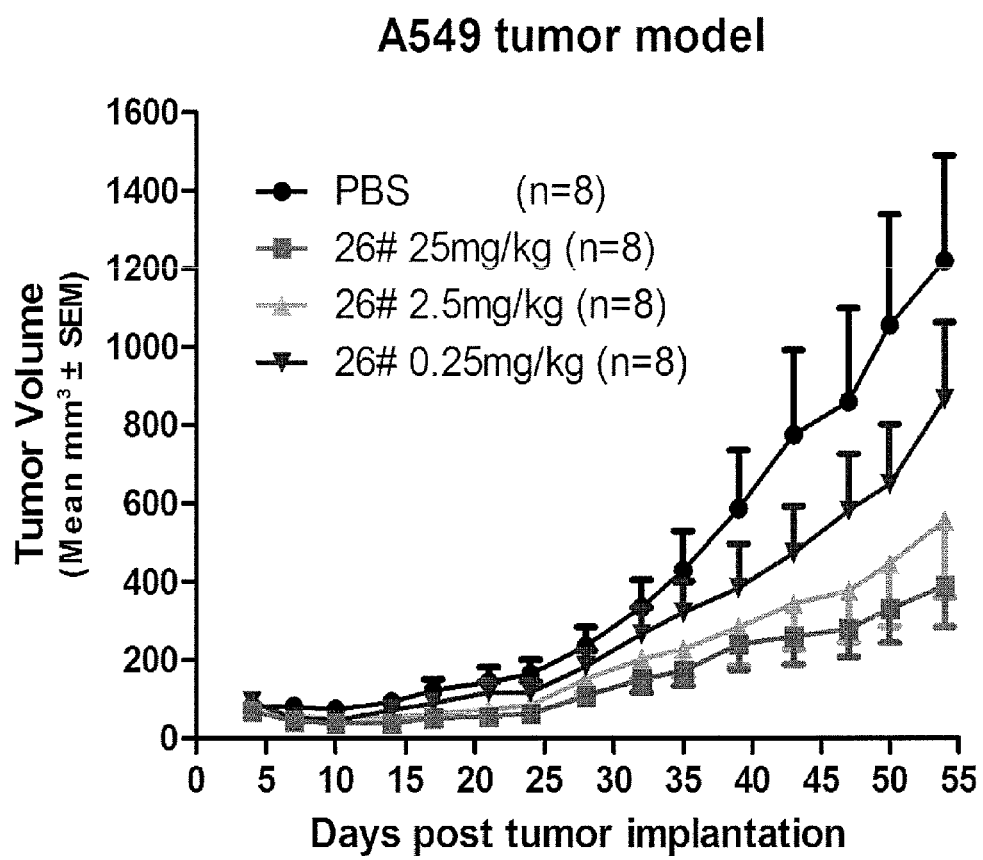
FIG. 8 shows the anti-tumor efficacy of FGFR-Fc in lung carcinoma model

Effect of FGFR-Fc (#26 fusion protein) on Caki-1 and A549 tumor growth in vivo. Caki-1 cells ($2 \times 10^6$; A) and A549 cells ($5 \times 10^6$; B) were s.c. injected into BALB/c nu/nu mice. FGFR-Fc blocked the growth of indicated s.c. implanted tumors, at the indicated doses twice weekly for 6 to 8 weeks. The tumor volumes [(length×width×width)/2] were measured, error bars represent standard error of mean, n=6-8 mice/treatment group. The results are shown in FIG. 8.

The present invention has been illustrated by specific examples. However, it will be appreciated by a person of ordinary skill in the art that the present invention is not limited to the specific embodiments. Various changes and modifications may be made by a person of ordinary skill under the scope of the present invention, and each technical feature mentioned in the specification may be combined without departing from the spirit and scope of the invention. Such changes and modifications fall within the scope of the present invention.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] Hanahan D, Weinberg R A. The hallmarks of cancer. Cell, 2000, 100(1):57-70.
[2] Hanahan D, Folkman J. Patterns and emerging mechanisms of the angiogenic switch during tumorigenesis. Cell. 1996, 86:353-64.
[3] Ferrara N, Gerber H P, LeCouter J. The biology of VEGF and its receptors. Nat. Med. 2003, 9:669-76.
[4] Ferrara N. Vascular endothelial growth factor as a target for anticancer therapy. Oncologist. 2004, 1:2-10.
[5] Jenab-Wolcott J, Giantonio B J. Bevacizumab: current indications and future development for management of solid tumors. Expert Opin Biol Ther. 2009, 9(4):507-17.
[6] Summers J, Cohen M H, Keegan P, Pazdur R. FDA drug approval summary: bevacizumab plus interferon for advanced renal cell carcinoma. Oncologist. 2010, 15(1): 104-11.
[7] Hsu J Y, Wakelee H A. Monoclonal antibodies targeting vascular endothelial growth factor: current status and future challenges in cancer therapy. BioDrugs. 2009, 23(5):289-304.
[8] Krupitskaya Y, Wakelee H A. Ramucirumab, a fully human mAb to the transmembrane signaling tyrosine kinase VEGFR-2 for the potential treatment of cancer. Curr Opin Investig Drugs. 2009, 10(6):597-605.
[9] Hurwitz H, Fehrenbacher L, Novotny W, Cartwright T, Hainsworth J, Heim W, Berlin J, Baron A, Griffing S, Holmgren E, Ferrara N, Fyfe G, Rogers B, Ross R, Kabbinavar F. Bevacizumab plus irinotecan, fluorouracil, and leucovorin for metastatic colorectal cancer. N Engl J. Med. 2004, 350(23):2335-42.

[10] Sandler A, Gray R, Perry M C, Brahmer J, Schiller J H, Dowlati A, Lilenbaum R, Johnson D H. Paclitaxel-carboplatin alone or with bevacizumab for non-small-cell lung cancer. N Engl J. Med. 2006, 355(24):2542-50.

[11] Jenab-Wolcott J, Giantonio Bevacizumab: current indications and future development for management of solid tumors. Expert Opin Biol Ther, 2009, 9(4):507-17.

[12] Donerrell M I, Aguilar E, Scheppke L, Barnett F H, Friedlander M. Combination angiostatic therapy completely inhibits ocular and tumor angiogenesis. Proc Natl Acad Sci USA. 2007, 104(3):967-72.

[13] Casanovas O, Hicklin D J, Bergers G, Hanahan D. Drug resistance by evasion of antiangiogenic targeting of VEGF signaling in late-stage pancreatic islet tumors. Cancer Cell. 2005, 8(4):299-309.

[14] A Beenken, M Mohammadi. Nature Rev., 2009, 8(3): 235~53.

[15] M Mohammadi, S K Olsen, O A Ibrahimi. Cytokine, 2005, 16: 107~137.

[16] M Presta, P D Era, S Mitola et al. Cytokine, 2005, 16(2): 159~178.

[17] R Grose, C Dickson. Cytokine, 2005, 16(2): 179~186.

[18] Y H Cao, R H Cao, E M Hedlund. J. Mol. Med., 2008, 86(7): 785~789.

[19] M J Cross, L C Welsh. Trends Pharmacol. Sci., 2001, 22(4): 201~207.

[20] Wang F. et al., J Biol. Chem. 1995, 270:10231-10235

[21] Olsen S K. et al., Proc Natl Acad Sci USA. 2004, 101: 935-940

[22] Gauglhofer C, Sagmeister S, Schrottmaier W, Fischer C, Rodgarkia-Dara C, Mohr T, Stattner S, Bichler C, Kandioler D, Wrba F, Schulte-Hermann R, Holzmann K, Grusch M, Marian B, Berger W, Grasl-Kraupp B. Hepatology. 2011 March; 53(3):854-64.

We claim:

1. An isolated soluble fusion protein comprising SEQ ID NO: 12.

2. An isolated soluble fusion protein comprising SEQ ID NO: 13.

3. An isolated soluble fusion protein comprising SEQ ID NO: 14.

4. The isolated soluble fusion protein, according to claim 1, which consists of SEQ. ID NO:12.

5. The isolated soluble fusion protein, according to claim 2, which consists of SEQ. ID NO:13.

6. The isolated soluble fusion protein, according to claim 3, which consists of SEQ. ID NO:14.

* * * * *

UNITED STATES PATENT AND TRADEMARK OFFICE
CERTIFICATE OF CORRECTION

PATENT NO. : 9,273,137 B2
APPLICATION NO. : 13/842345
DATED : March 1, 2016
INVENTOR(S) : Fang et al.

It is certified that error appears in the above-identified patent and that said Letters Patent is hereby corrected as shown below:

In the Specification

Column 1,
Line 45, "(HGF) etc." should read --(HGF) etc.,--.

Column 2,
Line 40, "Prof Hanahan's" should read --Prof. Hanahan's--.

Column 3,
Line 51, "a third ig-like" should read --a third Ig-like--.

Column 5,
Line 30, "Fe region" should read --Fc region--.

Column 12,
Line 63, ", edition," should read --, $2^{nd}$ edition,--.

Column 14,
Line 33, "2" edition" should read --$2^{nd}$ edition--.

Column 20,
Line 24, "B 16 melanoma" should read --B16 melanoma--.

Column 26,
Line 3, "300 PBST" should read --300μL PBST--.

Column 26,
Line 31, "deter mined" should read --determined--.

Signed and Sealed this
Twenty-first Day of June, 2016

Michelle K. Lee
*Director of the United States Patent and Trademark Office*

CERTIFICATE OF CORRECTION (continued)
U.S. Pat. No. 9,273,137 B2

Column 29,
Line 11, "[12] Donerrell MI" should read --[12] Dorrell MI--.

SEQUENCE LISTING

```
<160> NUMBER OF SEQ ID NOS: 33

<210> SEQ ID NO 1
<211> LENGTH: 820
<212> TYPE: PRT
<213> ORGANISM: Homo sapiens
<220> FEATURE:
<221> NAME/KEY: MISC_FEATURE
<222> LOCATION: (1)..(820)
<223> OTHER INFORMATION: amino acid sequence of human FGFR1
<220> FEATURE:
<221> NAME/KEY: MISC_FEATURE
<222> LOCATION: (40)..(118)
<223> OTHER INFORMATION: Ig1_FGFR
<220> FEATURE:
<221> NAME/KEY: MISC_FEATURE
<222> LOCATION: (163)..(247)
<223> OTHER INFORMATION: Ig2_FGFR
<220> FEATURE:
<221> NAME/KEY: MISC_FEATURE
<222> LOCATION: (270)..(359)
<223> OTHER INFORMATION: Ig3_FGFR

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160
```

```
Lys Lys Leu His Ala Val Pro Ala Ala Lys Thr Val Lys Phe Lys Cys
            165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
            195                 200                 205

Ala Thr Trp Ser Ile Ile Met Asp Ser Val Val Pro Ser Asp Lys Gly
            210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
            245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
            290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
            325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
            355                 360                 365

Ser Pro Leu Tyr Leu Glu Ile Ile Ile Tyr Cys Thr Gly Ala Phe Leu
            370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
            405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
            450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
            530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
            565                 570                 575
```

```
Pro Gly Leu Glu Tyr Cys Tyr Asn Pro Ser His Asn Pro Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
            645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
            690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
            725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
            770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
            805                 810                 815

Leu Lys Arg Arg
            820

<210> SEQ ID NO 2
<211> LENGTH: 1338
<212> TYPE: PRT
<213> ORGANISM: Homo sapiens
<220> FEATURE:
<221> NAME/KEY: MISC_FEATURE
<222> LOCATION: (1)..(1338)
<223> OTHER INFORMATION: amino acid sequence of human VEGFR1

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
            85                  90                  95

Ala Gln Ala Asn His Thr Gly Phe Tyr Ser Cys Lys Tyr Leu Ala Val
```

-continued

```
                100                 105                 110
Pro Thr Ser Lys Lys Glu Thr Glu Ser Ala Ile Tyr Ile Phe Ile
            115                 120                 125
Ser Asp Thr Gly Arg Pro Phe Val Glu Met Tyr Ser Glu Ile Pro Glu
            130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
            195                 200                 205
Ala Thr Val Asn Gly His Leu Tyr Lys Thr Asn Tyr Leu Thr His Arg
            210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
            275                 280                 285
Ala Asn Ile Phe Tyr Ser Val Leu Thr Ile Asp Lys Met Gln Asn Lys
            290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
            370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
            450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
            515                 520                 525
```

```
Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
                820                 825                 830

Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
                900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
930                 935                 940
```

```
Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335
```

-continued

```
<210> SEQ ID NO 3
<211> LENGTH: 1356
<212> TYPE: PRT
<213> ORGANISM: Homo sapiens
<220> FEATURE:
<221> NAME/KEY: MISC_FEATURE
<222> LOCATION: (1)..(1356)
<223> OTHER INFORMATION: amino acid sequence of human VEGFR2

<400> SEQUENCE: 3
```

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

-continued

```
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                    405                 410                 415
Val Tyr Val Pro Pro Gln Ile Gly Glu Lys Ser Leu Ile Ser Pro Val
                420                 425                 430
Asp Ser Tyr Gln Tyr Gly Thr Thr Gln Thr Leu Thr Cys Thr Val Tyr
            435                 440                 445
Ala Ile Pro Pro Pro His His Ile His Trp Tyr Trp Gln Leu Glu Glu
450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
                500                 505                 510
Thr Val Ser Thr Leu Val Ile Gln Ala Ala Asn Val Ser Ala Leu Tyr
            515                 520                 525
Lys Cys Glu Ala Val Asn Lys Val Gly Arg Gly Glu Arg Val Ile Ser
530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
            595                 600                 605
Leu Trp Lys Leu Asn Ala Thr Met Phe Ser Asn Ser Thr Asn Asp Ile
610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
            675                 680                 685
Thr Ala Ser Gly Asn Pro Pro Pro Gln Ile Met Trp Phe Lys Asp Asn
690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu Ile Ile Ile Leu
            755                 760                 765
Val Gly Thr Ala Val Ile Ala Met Phe Phe Trp Leu Leu Leu Val Ile
770                 775                 780
```

-continued

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
        930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu

```
                       1190                    1195                    1200
    Glu  Glu  Glu  Val  Cys  Asp  Pro  Lys  Phe  His  Tyr  Asp  Asn  Thr  Ala
        1205                    1210                    1215

Gly  Ile  Ser  Gln  Tyr  Leu  Gln  Asn  Ser  Lys  Arg  Lys  Ser  Arg  Pro
        1220                    1225                    1230

Val  Ser  Val  Lys  Thr  Phe  Glu  Asp  Ile  Pro  Leu  Glu  Pro  Glu
        1235                    1240                    1245

Val  Lys  Val  Ile  Pro  Asp  Asp  Asn  Gln  Thr  Asp  Ser  Gly  Met  Val
        1250                    1255                    1260

Leu  Ala  Ser  Glu  Glu  Leu  Lys  Thr  Leu  Glu  Asp  Arg  Thr  Lys  Leu
        1265                    1270                    1275

Ser  Pro  Ser  Phe  Gly  Gly  Met  Val  Pro  Ser  Lys  Ser  Arg  Glu  Ser
        1280                    1285                    1290

Val  Ala  Ser  Glu  Gly  Ser  Asn  Gln  Thr  Ser  Gly  Tyr  Gln  Ser  Gly
        1295                    1300                    1305

Tyr  His  Ser  Asp  Asp  Thr  Asp  Thr  Thr  Val  Tyr  Ser  Ser  Glu  Glu
        1310                    1315                    1320

Ala  Glu  Leu  Leu  Lys  Leu  Ile  Glu  Ile  Gly  Val  Gln  Thr  Gly  Ser
        1325                    1330                    1335

Thr  Ala  Gln  Ile  Leu  Gln  Pro  Asp  Ser  Gly  Thr  Thr  Leu  Ser  Ser
        1340                    1345                    1350

Pro  Pro  Val
        1355

<210> SEQ ID NO 4
<211> LENGTH: 5911
<212> TYPE: DNA
<213> ORGANISM: Homo sapiens
<220> FEATURE:
<221> NAME/KEY: misc_feature
<222> LOCATION: (1)..(5911)
<223> OTHER INFORMATION: nucleotide sequence of human FGFR1 (CDS:
      943-3405)

<400> SEQUENCE: 4
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc aggggggcgga ggcggaggag ggaccagcgc gggtggggagt gagagagcga     180 gccctcgcgc cccgccggcg catagcgctc ggagcgctct tgcggccaca ggcgcggcgt     240
cctcggcggc gggcggcagc tagcgggagc cgggacgccg gtgcagccgc agcgcgcgga     300
ggaacccggg tgtgccggga gctgggcggc cacgtccgga cgggaccgag acccctcgta     360
gcgcattgcg gcgaccctcg cttccccggc cgcgagcgcg ccgctgcttg aaaagccgcg     420
gaacccaagg acttttctcc ggtccgagct cggggcgccc cgcagggcgc acggtacccg     480
tgctgcagtc gggcacgccg cggcgccggg gcctccgcag ggcgatggag cccgtctgc      540 aaggaaagtg aggcgccgcc gctgcgttct ggaggagggg gcacaaggt ctggagaccc      600 cgggtggcgg acgggagccc tccccccgcc ccgcctccgg ggcaccagct ccggctccat     660
tgttcccgcc cgggctggag gcgccgagca ccgagcgccg ccgggagtcg agcgccggcc     720
gcggagctct tgcgaccccg ccaggacccg aacagagccc gggggcggcg ggccggagcc     780
ggggacgcgg gcacacgccc gctcgcacaa gccacggcgg actctcccga ggcggaacct     840
ccacgccgag cgagggtcag tttgaaaagg aggatcgagc tcactgtgga gtatccatgg     900
agatgtggag ccttgtcacc aacctctaac tgcagaactg ggatgtggag ctggaagtgc     960
```

```
ctcctcttct gggctgtgct ggtcacagcc acactctgca ccgctaggcc gtccccgacc    1020
ttgcctgaac aagcccagcc ctggggagcc cctgtggaag tggagtcctt cctggtccac    1080
cccggtgacc tgctgcagct tcgctgtcgg ctgcgggacg atgtgcagag catcaactgg    1140
ctgcgggacg gggtgcagct ggcggaaagc aaccgcaccc gcatcacagg ggaggaggtg    1200
gaggtgcagg actccgtgcc cgcagactcc ggcctctatg cttgcgtaac cagcagcccc    1260
tcgggcagtg acaccaccta cttctccgtc aatgtttcag atgctctccc ctcctcggag    1320
gatgatgatg atgatgatga ctcctcttca gaggagaaag aaacagataa caccaaacca    1380
aaccccgtag ctccatattg gacatcccca gaaaagatgg aaaagaaatt gcatgcagtg    1440
ccggctgcca agacagtgaa gttcaaatgc cttccagtg ggaccccaaa ccccacactg    1500
cgctggttga aaaatggcaa agaattcaaa cctgaccaca gaattggagg ctacaaggtc    1560
cgttatgcca cctggagcat cataatggac tctgtggtgc cctctgacaa gggcaactac    1620
acctgcattg tggagaatga gtacggcagc atcaaccaca cataccagct ggatgtcgtg    1680
gagcggtccc ctcaccggcc catcctgcaa gcagggttgc ccgccaacaa aacagtggcc    1740
ctgggtagca acgtggagtt catgtgtaag gtgtacagtg acccgcagcc gcacatccag    1800
tggctaaagc acatcgaggt gaatgggagc aagattggcc cagacaacct gccttatgtc    1860
cagatcttga agactgctgg agttaatacc accgacaaag atgaggt gcttcactta    1920 agaaatgtct cctttgagga cgcaggggag tatacgtgct ggcgggtaa ctctatcgga    1980 ctctcccatc actctgcatg gttgaccgtt ctggaagccc tggaagagag gccggcagtg    2040
atgacctcgc ccctgtacct ggagatcatc atctattgca caggggcctt cctcatctcc    2100
tgcatggtgg ggtcggtcat cgtctacaag atgaagagtg gtaccaagaa gagtgacttc    2160
cacagccaga tggctgtgca aagctggcc aagagcatcc ctctgcgcag acaggtaaca    2220
gtgtctgctg actccagtgc atccatgaac tctggggttc ttctggttcg gccatcacgg    2280
ctctcctcca gtgggactcc catgctagca ggggtctctg agtatgagct tcccgaagac    2340
cctcgctggg agctgcctcg ggacagactg gtcttaggca aacccctggg agagggctgc    2400
tttgggcagg tggtgttggc agaggctatc gggctgaca aggacaaacc caaccgtgtg    2460
accaaagtgg ctgtgaagat gttgaagtcg gacgcaacag agaaagactt gtcagacctg    2520
atctcagaaa tggagatgat gaagatgatc gggaagcata agaatatcat caacctgctg    2580
ggggcctgca cgcaggatgg tccttgtat gtcatcgtgg agtatgcctc caagggcaac    2640
ctgcgggagt acctgcaggc ccggaggccc ccagggctgg aatactgcta caaccccagc    2700
cacaacccag aggagcagct ctcctccaag gacctggtgt cctgcgccta ccaggtggcc    2760
cgaggcatga gtatctggc ctccaagaag tgcatacacc gagacctggc agccaggaat    2820
gtcctggtga cagaggacaa tgtgatgaag atagcagact ttggcctcgc acgggacatt    2880
caccacatcg actactataa aaagacaacc aacggccgac tgcctgtgaa gtggatggca    2940
cccgaggcat tatttgaccg gatctacacc caccagagtg atgtgtggtc tttcggggtg    3000
ctcctgtggg agatcttcac tctgggcggc tccccatacc ccggtgtgcc tgtggaggaa    3060
cttttcaagc tgctgaagga gggtcaccgc atggacaagc cagtaactg caccaacgag    3120 ctgtacatga tgatgcggga ctgctggcat gcagtgccct cacagagacc caccttcaag    3180
cagctggtgg aagacctgga ccgcatcgtg gccttgacct ccaaccagga gtacctggac    3240
ctgtccatgc ccctggacca gtactccccc agctttcccg acacccggag ctctacgtgc    3300
```

```
tcctcagggg aggattccgt cttctctcat gagccgctgc ccgaggagcc ctgcctgccc    3360
cgacacccag cccagcttgc caatggcgga ctcaaacgcc gctgactgcc acccacacgc    3420
cctccccaga ctccaccgtc agctgtaacc ctcacccaca gccctgctg ggcccaccac     3480
ctgtccgtcc ctgtccccct tcctgctggc aggagccggc tgcctaccag gggccttcct    3540
gtgtggcctg ccttcacccc actcagctca cctctccctc cacctcctct ccacctgctg    3600
gtgagaggtg caaagaggca gatctttgct gccagccact tcatcccctc ccagatgttg    3660
gaccaacacc cctccctgcc accaggcact gcctggaggg cagggagtgg gagccaatga    3720
acaggcatgc aagtgagagc ttcctgagct ttctcctgtc ggtttggtct gttttgcctt    3780
cacccataag cccctcgcac tctggtggca ggtgccttgt cctcagggct acagcagtag    3840
ggaggtcagt gcttcgtgcc tcgattgaag gtgacctctg ccccagatag gtggtgccag    3900
tggcttatta attccgatac tagtttgctt tgctgaccaa atgcctggta ccagaggatg    3960
gtgaggcgaa ggccaggttg ggggcagtgt tgtggccctg ggcccagcc ccaaactggg      4020
ggctctgtat atagctatga agaaaacaca aagtgtataa atctgagtat atatttacat    4080
gtcttttttaa aagggtcgtt accagagatt tacccatcgg gtaagatgct cctggtggct    4140
gggaggcatc agttgctata tattaaaaac aaaaaagaaa aaaaaggaaa atgttttttaa   4200
aaaggtcata tatttttttgc tacttttgct gtttttatttt tttaaattat gttctaaacc  4260
tattttcagt ttaggtccct caataaaaat tgctgctgct tcatttatct atgggctgta   4320
tgaaaagggt gggaatgtcc actggaaaga agggacaccc acgggccctg gggctaggtc   4380
tgtcccgagg gcaccgcatg ctcccggcgc aggttccttg taacctcttc ttcctaggtc   4440
ctgcacccag acctcacgac gcacctcctg cctctccgct gcttttggaa agtcagaaaa   4500
agaagatgtc tgcttcgagg gcaggaaccc catccatgca gtagaggcgc tgggcagaga   4560
gtcaaggccc agcagccatc gaccatggat ggtttcctcc aaggaaaccg gtggggttgg   4620
gctggggagg gggcacctac ctaggaatag ccacggggta gagctacagt gattaagagg   4680
aaagcaaggg cgcggttgct cacgcctgta atcccagcac tttgggacac cgaggtgggc   4740
agatcacttc aggtcaggag tttgagacca gcctggccaa cttagtgaaa ccccatctct   4800
actaaaaatg caaaaattat ccaggcatgg tggcacacgc ctgtaatccc agctccacag   4860
gaggctgagg cagaatccct tgaagctggg aggcggaggt tgcagtgagc cgagattgcg   4920
ccattgcact ccagcctggg caacagagaa acaaaaagg aaaacaaatg atgaaggtct    4980
gcagaaactg aaacccagac atgtgtctgc cccctctatg tgggcatggt tttgccagtg   5040
cttctaagtg caggagaaca tgtcacctga ggctagtttt gcattcaggt ccctggcttc   5100
gtttcttgtt ggtatgcctc cccagatcgt ccttcctgta tccatgtgac cagactgtat   5160
ttgttgggac tgtcgcagat cttggcttct tacagttctt cctgtccaaa ctccatcctg   5220
tccctcagga acgggggaa aattctccga atgttttttgg ttttttggct gcttggaatt    5280
tacttctgcc acctgctggt catcactgtc ctcactaagt ggattctggc tccccgtac    5340
ctcatggctc aaactaccac tcctcagtcg ctatattaaa gcttatattt tgctggatta   5400
ctgctaaata caaagaaag ttcaatatgt tttcatttct gtaggaaaaa tgggattgct    5460
gctttaaatt tctgagctag ggatttttg gcagctgcag tgttggcgac tattgtaaaa    5520
ttctcttttgt ttctctctgt aaatagcacc tgctaacatt acaatttgta tttatgttta   5580
aagaaggcat catttggtga acagaactag gaaatgaatt tttagctctt aaaagcattt    5640
gctttgagac cgcacaggag tgtctttcct tgtaaaacag tgatgataat ttctgccttg   5700
```

| gccctacctt gaagcaatgt tgtgtgaagg gatgaagaat ctaaaagtct tcataagtcc | 5760 |
| ttgggagagg tgctagaaaa atataaggca ctatcataat tacagtgatg tccttgctgt | 5820 |
| tactactcaa atcacccaca aatttcccca aagactgcgc tagctgtcaa ataaaagaca | 5880 |
| gtgaaattga cctgaaaaaa aaaaaaaaaa a | 5911 |

```
<210> SEQ ID NO 5
<211> LENGTH: 7123
<212> TYPE: DNA
<213> ORGANISM: Homo sapiens
<220> FEATURE:
<221> NAME/KEY: misc_feature
<222> LOCATION: (1)..(7123)
<223> OTHER INFORMATION: nucleotide sequence of human VEGFR1 (CDS:
      286-4302)

<400> SEQUENCE: 5
```

| atcgaggtcc gcgggaggct cggagcgcgc caggcggaca ctcctctcgg ctcctccccg | 60 |
| gcagcggcgg cggctcggag cgggctccgg ggctcgggtg cagcggccag cgggcgcctg | 120 |
| gcggcgagga ttacccgggg aagtggttgt ctcctggctg gagccgcgag acgggcgctc | 180 |
| agggcgcggg gccggcggcg gcgaacgaga ggacggactc tggcggccgg gtcgttggcc | 240 |
| gcggggagcg cgggcaccgg gcgagcaggc cgcgtcgcgc tcaccatggt cagctactgg | 300 |
| gacaccgggg tcctgctgtg cgcgctgctc agctgtctgc ttctcacagg atctagttca | 360 |
| ggttcaaaat taaaagatcc tgaactgagt ttaaaaggca cccagcacat catgcaagca | 420 |
| ggccagacac tgcatctcca atgcaggggg gaagcagccc ataaatggtc tttgcctgaa | 480 |
| atggtgagta aggaaagcga aaggctgagc ataactaaat ctgcctgtgg aagaaatggc | 540 |
| aaacaattct gcagtacttt aaccttgaac acagctcaag caaaccacac tggcttctac | 600 |
| agctgcaaat atctagctgt acctacttca aagaagaagg aaacagaatc tgcaatctat | 660 |
| atatttatta gtgatacagg tagaccttc gtagagatgt acagtgaaat ccccgaaatt | 720 |
| atacacatga ctgaaggaag ggagctcgtc attccctgcc gggttacgtc acctaacatc | 780 |
| actgttactt aaaaaagtt tccacttgac actttgatcc ctgatggaaa acgcataatc | 840 |
| tgggacagta gaaagggctt catcatatca aatgcaacgt acaaagaaat agggcttctg | 900 |
| acctgtgaag caacagtcaa tgggcatttg tataagacaa actatctcac acatcgacaa | 960 |
| accaatacaa tcatagatgt ccaaataagc acaccacgcc cagtcaaatt acttagaggc | 1020 |
| catactcttg tcctcaattg tactgctacc actcccttga acacgagagt tcaaatgacc | 1080 |
| tggagttacc ctgatgaaaa aaataagaga gcttccgtaa ggcgacgaat tgaccaaagc | 1140 |
| aattcccatg ccaacatatt ctacagtgtt cttactattg acaaaatgca gaacaaagac | 1200 |
| aaaggacttt atacttgtcg tgtaaggagt ggaccatcat tcaaatctgt taacacctca | 1260 |
| gtgcatatat atgataaagc attcatcact gtgaaacatc gaaaacagca ggtgcttgaa | 1320 |
| accgtagctg gcaagcggtc ttaccggctc tctatgaaag tgaaggcatt ccctcgcccg | 1380 |
| gaagttgtat ggttaaaaga tgggttacct gcgactgaga atctgctcg ctatttgact | 1440 |
| cgtggctact cgttaattat caaggacgta actgaagagg atgcagggaa ttatacaatc | 1500 |
| ttgctgagca taaaacagtc aaatgtgttt aaaaacctca ctgccactct aattgtcaat | 1560 |
| gtgaaacccc agatttacga aaaggccgtg tcatcgtttc cagacccggc tctctaccca | 1620 |
| ctgggcagca gacaaatcct gacttgtacc gcatatggta tccctcaacc tacaatcaag | 1680 |
| tggttctggc acccctgtaa ccataatcat tccgaagcaa ggtgtgactt tgttccaat | 1740 |

```
aatgaagagt cctttatcct ggatgctgac agcaacatgg gaaacagaat tgagagcatc    1800
actcagcgca tggcaataat agaaggaaag aataagatgg ctagcacctt ggttgtggct    1860
gactctagaa tttctggaat ctacatttgc atagcttcca ataaagttgg gactgtggga    1920
agaaacataa gcttttatat cacagatgtg ccaaatgggt ttcatgttaa cttggaaaaa    1980
atgccgacgg aaggagagga cctgaaactg tcttgcacag ttaacaagtt cttatacaga    2040
gacgttactt ggattttact gcggacagtt aataacagaa caatgcacta cagtattagc    2100
aagcaaaaaa tggccatcac taaggagcac tccatcactc ttaatcttac catcatgaat    2160
gtttccctgc aagattcagg cacctatgcc tgcagagcca ggaatgtata cacaggggaa    2220
gaaatcctcc agaagaaaga aattacaatc agagatcagg aagcaccata cctcctgcga    2280
aacctcagtg atcacacagt ggccatcagc agttccacca ctttagactg tcatgctaat    2340
ggtgtccccg agcctcagat cacttggttt aaaaacaacc acaaaataca caagagcct     2400
ggaattattt taggaccagg aagcagcacg ctgtttattg aaaagagtca c agaagaggat   2460
gaaggtgtct atcactgcaa agccaccaac cagaagggct ctgtggaaag ttcagcatac    2520
ctcactgttc aaggaacctc ggacaagtct aatctggagc tgatcactct aacatgcacc    2580
tgtgtggctg cgactctctt ctggctccta ttaaccctct ttatccgaaa atgaaaagg     2640
tcttcttctg aaataaagac tgactaccta tcaattataa tggacccaga tgaagttcct    2700
ttggatgagc agtgtgagcg gctcccttat gatgccagca gtgggagtt tgcccgggag     2760
agacttaaac tgggcaaatc acttggaaga ggggcttttg aaaagtggt tcaagcatca     2820
gcatttggca ttaagaaatc acctacgtgc cggactgtgg ctgtgaaaat gctgaaagag    2880
gggaccacgg ccagcgagta caaagctctg atgactgagc taaaaatctt gacccacatt    2940
ggccaccatc tgaacgtggt taacctgctg ggagcctgca ccaagcaagg agggcctctg    3000
atggtgattg ttgaatactg caaatatgga aatctctcca actacctcaa gagcaaacgt    3060
gacttatttt ttctcaacaa ggatgcagca ctacacatgg agcctaagaa agaaaaaatg    3120
gagccaggcc tggaacaagg caagaaacca agactagata gcgtcaccag cagcgaaagc    3180
tttgcgagct ccggctttca ggaagataaa gtctgagtg atgttgagga agaggaggat    3240
tctgacggtt tctacaagga gcccatcact atggaagatc tgatttctta cagttttcaa    3300
gtggccagag gcatggagtt cctgtcttcc agaaagtgca ttcatcggga cctggcagcg    3360
agaaacattc ttttatctga gaacaacgtg gtgaagattt gtgattttgg ccttgcccgg    3420
gatatttata gaaccccga ttatgtgaga aaaggagata ctcgacttcc tctgaaatgg    3480
atggctcctg aatctatctt tgacaaaatc tacagcacca gagcgacgt gtggtcttac    3540
ggagtattgc tgtgggaaat cttctcctta ggtgggtctc catacccagg agtacaaatg    3600
gatgaggact tttgcagtcg cctgagggaa ggcatgagga tgagagctcc tgagtactct    3660
actcctgaaa tctatcagat catgctggac tgctggcaca gagacccaaa agaaaggcca    3720
agatttgcag aacttgtgga aaactaggt gatttgcttc aagcaaatgt acaacaggat    3780
ggtaaagact acatcccaat caatgccata ctgacaggaa atagtgggtt tacatactca    3840
actcctgcct tctctgagga cttcttcaag gaaagtattt cagctccgaa gtttaattca    3900
ggaagctctg atgatgtcag atacgtaaat gctttcaagt tcatgagcct ggaaagaatc    3960
aaaacctttg aagaactttt accgaatgcc acctccatgt ttgatgacta ccagggcgac    4020
agcagcactc tgttggcctc tcccatgctg aagcgcttca cctggactga cagcaaaccc    4080
```

```
aaggcctcgc tcaagattga cttgagagta accagtaaaa gtaaggagtc ggggctgtct    4140
gatgtcagca ggcccagttt ctgccattcc agctgtgggc acgtcagcga aggcaagcgc    4200
aggttcacct acgaccacgc tgagctggaa aggaaaatcg cgtgctgctc cccgccccca    4260
gactacaact cggtggtcct gtactccacc ccaccatct agagtttgac acgaagcctt    4320
atttctagaa gcacatgtgt atttataccc ccaggaaact agcttttgcc agtattatgc    4380
atatataagt ttacacccttt atcttttccat gggagccagc tgcttttttgt gattttttta    4440 atagtgcttt ttttttttttg actaacaaga atgtaactcc agatagagaa atagtgacaa    4500
gtgaagaaca ctactgctaa atcctcatgt tactcagtgt tagagaaatc cttcctaaac    4560
ccaatgactt ccctgctcca accccgcca cctcagggca cgcaggacca gtttgattga    4620
ggagctgcac tgatcaccca atgcatcacg taccccactg gccagccct gcagcccaaa    4680 acccagggca acaagcccgt tagccccagg gatcactggc tggcctgagc aacatctcgg    4740
gagtcctcta gcaggcctaa gacatgtgag gaggaaaagg aaaaaaagca aaaagcaagg    4800
gagaaaagag aaaccgggag aaggcatgag aaagaatttg agacgcacca tgtgggcacg    4860 gaggggacg gggctcagca atgccatttc agtggcttcc cagctctgac ccttctacat    4920
ttgagggccc agccaggagc agatggacag cgatgagggg acattttctg gattctggga    4980
ggcaagaaaa ggacaaatat cttttttgga actaaagcaa attttagaac tttacctatg    5040
gaagtggttc tatgtccatt ctcattcgtg gcatgttttg atttgtagca ctgagggtgg    5100
cactcaactc tgagcccata cttttggctc tctagtaag atgcactgaa aacttagcca    5160
gagttaggtt gtctccaggc catgatggcc ttacactgaa aatgtcacat tctatttttgg   5220 gtattaatat atagtccaga cacttaactc aatttcttgg tattattctg ttttgcacag    5280
ttagttgtga aagaaagctg agaagaatga aaatgcagtc ctgaggagag gagttttctc    5340
catatcaaaa cgagggctga tggaggaaaa aggtcaataa ggtcaaggga aaaccccgtc    5400
tctataccaa ccaaaccaat tcaccaacac agttgggacc caaaacacag gaagtcagtc    5460
acgtttcctt ttcatttaat ggggattcca ctatctcaca ctaatctgaa aggatgtgga    5520
agagcattag ctggcgcata ttaagcactt taagctcctt gagtaaaaag gtggtatgta    5580
atttatgcaa ggtatttctc cagttgggac tcaggatatt agttaatgag ccatcactag    5640
aagaaaagcc cattttcaac tgctttgaaa cttgcctggg gtctgagcat gatgggaata    5700
gggagacagg gtaggaaagg gcgcctactc ttcagggtct aaagatcaag tgggccttgg    5760
atcgctaagc tggctctgtt tgatgctatt tatgcaagtt agggtctatg tatttatgat    5820
gtctgcacct tctgcagcca gtcagaagct ggagaggcaa cagtggattg ctgcttcttg    5880
gggagaagag tatgcttcct tttatccatg taatttaact gtagaacctg agctctaagt    5940
aaccgaagaa tgtatgcctc tgttcttatg tgccacatcc ttgtttaaag gctctctgta    6000
tgaagagatg ggaccgtcat cagcacattc cctagtgagc ctactggctc ctggcagcgg    6060
cttttgtgga agactcacta gccagaagag aggagtggga cagtcctctc caccaagatc    6120
taaatccaaa caaaagcagg ctagagccag aagagaggac aaatctttgt tcttcctctt    6180
ctttacatac gcaaaccacc tgtgacagct ggcaatttta taaatcaggt aactggaagg    6240
aggttaaaca cagaaaaaag aagacctcag tcaattctct acttttttttt tttttttccaa    6300 atcagataat agcccagcaa atagtgataa caaataaaac cttagctatt catgtcttga    6360
tttcaataat taattcttaa tcattaagag accataataa atactccttt tcaagagaaa    6420
agcaaaacca ttagaattgt tactcagctc cttcaaactc aggtttgtag catacatgag    6480
```

| | | |
|---|---|---|
| tccatccatc agtcaaagaa tggttccatc tggagtctta atgtagaaag aaaaatggag | 6540 | |
| acttgtaata atgagctagt tacaaagtgc ttgttcatta aaatagcact gaaaattgaa | 6600 | |
| acatgaatta actgataata ttccaatcat ttgccattta tgacaaaaat ggttggcact | 6660 | |
| aacaaagaac gagcacttcc tttcagagtt tctgagataa tgtacgtgga acagtctggg | 6720 | |
| tggaatgggg ctgaaaccat gtgcaagtct gtgtcttgtc agtccaagaa gtgacaccga | 6780 | |
| gatgttaatt ttagggaccc gtgccttgtt tcctagccca caagaatgca aacatcaaac | 6840 | |
| agatactcgc tagcctcatt taaattgatt aaaggaggag tgcatctttg gccgacagtg | 6900 | |
| gtgtaactgt atgtgtgtgt gtgtgtgtgt gtgtgtgtgt gtgtgtgggt gtatgtgtgt | 6960 | |
| tttgtgcata actatttaag gaaactggaa ttttaaagtt acttttatac aaaccaagaa | 7020 | |
| tatatgctac agatataaga cagacatggt ttggtcctat atttctagtc atgatgaatg | 7080 | |
| tattttgtat accatcttca tataataaac ttccaaaaac aca | 7123 | |

<210> SEQ ID NO 6
<211> LENGTH: 6055
<212> TYPE: DNA
<213> ORGANISM: Homo sapiens
<220> FEATURE:
<221> NAME/KEY: misc_feature
<222> LOCATION: (1)..(6055)
<223> OTHER INFORMATION: nucleotide sequence of human VEGFR2 (CDS: 303-4373)

<400> SEQUENCE: 6

| | | |
|---|---|---|
| actgagtccc gggaccccgg gagagcggtc aatgtgtggt cgctgcgttt cctctgcctg | 60 | |
| cgccgggcat cacttgcgcg ccgcagaaag tccgtctggc agcctggata tcctctccta | 120 | |
| ccggcacccg cagacgcccc tgcagccgcg gtcggcgccc gggctcccta gccctgtgcg | 180 | |
| ctcaactgtc ctgcgctgcg gggtgccgcg agttccacct ccgcgcctcc ttctctagac | 240 | |
| aggcgctggg agaaagaacc ggctcccgag ttctgggcat ttcgcccggc tcgaggtgca | 300 | |
| ggatgcagag caaggtgctg ctggccgtcg ccctgtggct ctgcgtggag acccgggccg | 360 | |
| cctctgtggg tttgcctagt gtttctcttg atctgcccag gctcagcata caaaaagaca | 420 | |
| tacttacaat taaggctaat acaactcttc aaattacttg caggggacag agggacttgg | 480 | |
| actggctttg gcccaataat cagagtggca gtgagcaaag ggtggaggtg actgagtgca | 540 | |
| gcgatggcct cttctgtaag acactcacaa ttccaaaagt gatcggaaat gacactggag | 600 | |
| cctacaagtg cttctaccgg gaaactgact tggcctcggt catttatgtc tatgttcaag | 660 | |
| attacagatc tccatttatt gcttctgtta gtgaccaaca tggagtcgtg tacattactg | 720 | |
| agaacaaaaa caaaactgtg gtgattccat gtctcgggtc catttcaaat ctcaacgtgt | 780 | |
| cactttgtgc aagataccca gaaaagagat tgttcctga tggtaacaga atttcctggg | 840 | |
| acagcaagaa gggctttact attcccagct acatgatcag ctatgctggc atggtcttct | 900 | |
| gtgaagcaaa aattaatgat gaaagttacc agtctattat gtacatagtt gtcgttgtag | 960 | |
| ggtataggat ttatgatgtg gttctgagtc cgtctcatgg aattgaacta tctgttggag | 1020 | |
| aaaagcttgt cttaaattgt acagcaagaa ctgaactaaa tgtggggatt gacttcaact | 1080 | |
| gggaataccc ttcttcgaag catcagcata aaaaacttgt aaaccgagac ctaaaaaccc | 1140 | |
| agtctgggag tgagatgaag aaattttga gcaccttaac tatagatggt gtaacccgga | 1200 | |
| gtgaccaagg attgtacacc tgtgcagcat ccagtgggct gatgaccaag aagaacagca | 1260 | |
| catttgtcag ggtccatgaa aaaccttttg ttgcttttgg aagtggcatg gaatctctgg | 1320 | |

```
tggaagccac ggtgggggag cgtgtcagaa tccctgcgaa gtaccttggt tacccacccc    1380
cagaaataaa atggtataaa aatggaatac cccttgagtc caatcacaca attaaagcgg    1440
ggcatgtact gacgattatg gaagtgagtg aaagagacac aggaaattac actgtcatcc    1500
ttaccaatcc catttcaaag gagaagcaga gccatgtggc tctctctggtt gtgtatgtcc    1560 caccccagat tggtgagaaa tctctaatct ctcctgtgga ttcctaccag tacggcacca    1620
ctcaaacgct gacatgtacg gtctatgcca ttcctcccccc gcatcacatc cactggtatt    1680
ggcagttgga ggaagagtgc gccaacgagc ccagccaagc tgtctcagtg acaaacccat    1740
acccttgtga agaatggaga agtgtggagg acttccaggg aggaaataaa attgaagtta    1800
ataaaaatca atttgctcta attgaaggaa aaacaaaac tgtaagtacc cttgttatcc    1860
aagcggcaaa tgtgtcagct ttgtacaaat gtgaagcgt caacaaagtc gggagaggag    1920
agagggtgat ctccttccac gtgaccaggg gtcctgaaat tactttgcaa cctgacatgc    1980
agcccactga gcaggagagc gtgtctttgt ggtgcactgc agacagatct acgtttgaga    2040
acctcacatg gtacaagctt ggcccacagc ctctgccaat ccatgtggga gagttgccca    2100
cacctgtttg caagaacttg gatactcttt ggaaattgaa tgccaccatg ttctctaata    2160
gcacaaatga cattttgatc atggagctta agaatgcatc cttgcaggac caaggagact    2220
atgtctgcct tgctcaagac aggaagacca agaaaagaca ttgcgtggtc aggcagctca    2280
cagtcctaga gcgtgtggca cccacgatca caggaaacct ggagaatcag acgacaagta    2340
ttggggaaag catcgaagtc tcatgcacgg catctgggaa tccccctcca cagatcatgt    2400
ggtttaaaga taatgagacc cttgtagaag actcaggcat tgtattgaag gatgggaacc    2460
ggaacctcac tatccgcaga gtgaggaagg aggacgaagg cctctacacc tgccaggcat    2520
gcagtgttct tggctgtgca aaagtggagg catttttcat aatagaaggt gcccaggaaa    2580
agacgaactt ggaaatcatt attctagtag gcacggcgt gattgccatg ttcttctggc    2640
tacttcttgt catcatccta cggaccgtta agcgggccaa tggaggggaa ctgaagacag    2700
gctacttgtc catcgtcatg gatccagatg aactcccatt ggatgaacat tgtgaacgac    2760
tgccttatga tgccagcaaa tgggaattcc ccagagaccg gctgaagcta ggtaagcctc    2820
ttggccgtgg tgcctttggc caagtgattg aagcagatgc ctttggaatt gacaagacag    2880
caacttgcag gacagtagca gtcaaaatgt gaaagaagg agcaacacac agtgagcatc    2940
gagctctcat gtctgaactc aagatcctca ttcatattgg tcaccatctc aatgtggtca    3000
accttctagg tgcctgtacc aagccaggag ggccactcat ggtgattgtg gaattctgca    3060
aatttggaaa cctgtccact tacctgagga gcaagagaaa tgaatttgtc ccctacaaga    3120 ccaaggggc acgattccgt caaggaaag actacgttgg agcaatccct gtggatctga    3180
aacggcgctt ggacagcatc accagtagcc agagctcagc cagctctgga tttgtggagg    3240
agaagtccct cagtgatgta gaagaagagg aagctcctga gatctgtat aaggacttcc    3300 tgaccttgga gcatctcatc tgttacagct tccaagtggc taagggcatg gagttcttgg    3360
catcgcgaaa gtgtatccac agggacctgg cggcacgaaa tatcctctta tcggagaaga    3420
acgtggttaa aatctgtgac tttggcttgg cccgggatat ttataaagat ccagattatg    3480
tcagaaaagg agatgctcgc ctcccctttga aatggatggc cccagaaaca atttttgaca    3540
gagtgtacac aatccagagt gacgtctggt cttttggtgt tttgctgtgg gaaatatttt    3600
ccttaggtgc ttctccatat cctggggtaa agattgatga agaattttgt aggcgattga    3660
```

```
aagaaggaac tagaatgagg gcccctgatt atactacacc agaaatgtac cagaccatgc    3720
tggactgctg gcacggggag cccagtcaga gacccacgtt ttcagagttg gtggaacatt    3780
tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
tcagtcagta tctgcagaac agtaagcgaa agagccggcc tgtgagtgta aaaacatttg    4020
aagatatccc gttagaagaa ccagaagtaa aagtaatccc agatgacaac cagacggaca    4080
gtggtatggt tcttgcctca gaagagctga aaactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
ccagtgagga agcagaactt ttaaagctga tagagattgg agtgcaaacc ggtagcacag    4320
cccagattct ccagcctgac tcggggacca cactgagctc tcctcctgtt taaaaggaag    4380
catccacacc cccaactcct ggacatcaca tgagaggtgc tgctcagatt ttcaagtgtt    4440 gttcttttcca ccagcaggaa gtagccgcat ttgattttca tttcgacaac agaaaaagga    4500
cctcggactg cagggagcca gtcttctagg catatcctgg aagaggcttg tgacccaaga    4560
atgtgtctgt gtcttctccc agtgttgacc tgatcctctt tttcattcat ttaaaaagca    4620
tttatcatgc cccctgctgc gggtctcacc atgggtttag aacaaagacg ttcaagaaat    4680
ggccccatcc tcaaagaagt agcagtacct ggggagctga cacttctgta aaactagaag    4740
ataaaccagg caatgtaagt gttcgaggtg ttgaagatgg gaaggatttg cagggctgag    4800
tctatccaag aggctttgtt taggacgtgg gtcccaagcc aagccttaag tgtggaattc    4860
ggattgatag aaaggaagac taacgttacc ttgctttgga gagtactgga gcctgcaaat    4920
gcattgtgtt tgctctggtg gaggtgggca tggggtctgt tctgaaatgt aaagggttca    4980 gacgggttt ctggttttag aaggttgcgt gttcttcgag ttgggctaaa gtagagttcg    5040
ttgtgctgtt tctgactcct aatgagagtt ccttccagac cgttacgtgt ctcctggcca    5100
agccccagga aggaaatgat gcagctctgg ctccttgtct cccaggctga tcctttattc    5160
agaataccac aaagaaagga cattcagctc aaggctccct gccgtgttga agagttctga    5220
ctgcacaaac cagcttctgg tttcttctgg aatgaatacc ctcatatctg tcctgatgtg    5280
atatgtctga gactgaatgc gggaggttca atgtgaagct gtgtgtggtg tcaaagtttc    5340
aggaaggatt ttaccctttt gttcttcccc ctgtccccaa cccactctca ccccgcaacc    5400
catcagtatt ttagttattt ggcctctact ccagtaaacc tgattgggtt tgttcactct    5460
ctgaatgatt attagccaga cttcaaaatt attttatagc ccaaattata acatctattg    5520
tattatttag acttttaaca tatagagcta tttctactga tttttgccct tgttctgtcc    5580 ttttttttcaa aaaagaaaat gtgttttttg tttggtacca tagtgtgaaa tgctgggaac    5640
aatgactata agacatgcta tggcacatat atttatagtc tgtttatgta gaaacaaatg    5700
taatatatta aagccttata tataatgaac tttgtactat tcacattttg tatcagtatt    5760
atgtagcata acaaaggtca taatgctttc agcaattgat gtcattttat taagaacat     5820 tgaaaaactt gaaggaatcc ctttgcaagg ttgcattact gtacccatca tttctaaaat    5880
ggaagagggg gtggctgggc acagtggccg acacctaaaa acccagcact tggggggcc     5940 aaggtgggag gatcgcttga gcccaggagt tcaagaccag tctggccaac atggtcagat    6000
tccatctcaa agaaaaaagg taaaaataaa ataaaatgga gaagaaggaa tcaga         6055
```

<210> SEQ ID NO 7
<211> LENGTH: 223
<212> TYPE: PRT
<213> ORGANISM: Homo sapiens
<220> FEATURE:
<221> NAME/KEY: MISC_FEATURE
<222> LOCATION: (1)..(223)
<223> OTHER INFORMATION: amino acid sequence of human IgG Fc

<400> SEQUENCE: 7

```
Thr Cys Pro Pro Cys Pro Ala Pro Glu Leu Leu Gly Gly Pro Ser Val
1               5                   10                  15
Phe Leu Phe Pro Pro Lys Pro Lys Asp Thr Leu Met Ile Ser Arg Thr
            20                  25                  30
Pro Glu Val Thr Cys Val Val Val Asp Val Ser His Glu Asp Pro Glu
        35                  40                  45
Val Lys Phe Asn Trp Tyr Val Asp Gly Val Glu Val His Asn Ala Lys
    50                  55                  60
Thr Lys Pro Arg Glu Glu Gln Tyr Asn Ser Thr Tyr Arg Val Val Ser
65                  70                  75                  80
Val Leu Thr Val Leu His Gln Asp Trp Leu Asn Gly Lys Glu Tyr Lys
                85                  90                  95
Cys Lys Val Ser Asn Lys Ala Leu Pro Ala Pro Ile Glu Lys Thr Ile
            100                 105                 110
Ser Lys Ala Lys Gly Gln Pro Arg Glu Pro Gln Val Tyr Thr Leu Pro
        115                 120                 125
Pro Ser Arg Asp Glu Leu Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Asp Ser
                165                 170                 175
Asp Gly Pro Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Ser Leu Ser Pro Gly Lys
    210                 215                 220
```

<210> SEQ ID NO 8
<211> LENGTH: 669
<212> TYPE: DNA
<213> ORGANISM: Homo sapiens
<220> FEATURE:
<221> NAME/KEY: misc_feature
<222> LOCATION: (1)..(669)
<223> OTHER INFORMATION: DNA sequence of human IgG FC

<400> SEQUENCE: 8

```
acatgcccac cgtgcccagc acctgaactc ctggggggac cgtcagtctt cctcttcccc      60
ccaaaaccca aggacaccct catgatctcc cggacccctg aggtcacatg cgtggtggtg     120
gacgtgagcc acgaagaccc tgaggtcaag ttcaactggt acgtggacgg cgtggaggtg     180
cataatgcca agacaaagcc gcgggaggag cagtacaaca gcacgtaccg tgtggtcagc     240
gtcctcaccg tcctgcacca ggactggctg aatggcaagg agtacaagtg caaggtctcc     300
aacaaagccc tcccagcccc catcgagaaa accatctcca aagccaaagg gcagcccga     360
```

```
gaaccacagg tgtacaccct gcccccatcc cgggatgagc tgaccaagaa ccaggtcagc    420
ctgacctgcc tggtcaaagg cttctatccc agcgacatcg ccgtggagtg ggagagcaat    480
gggcagccgg agaacaacta caagaccacg cctcccgtgc tggactccga cggccccttc    540
ttcctctaca gcaagctcac cgtggacaag agcaggtggc agcaggggaa cgtcttctca    600
tgctccgtga tgcatgaggc tctgcacaac cactacacgc agaagagcct ctccctgtct    660
ccgggtaaa                                                            669
```

```
<210> SEQ ID NO 9
<211> LENGTH: 580
<212> TYPE: PRT
<213> ORGANISM: Artificial sequence
<220> FEATURE:
<223> OTHER INFORMATION: #19 fusion protein

<400> SEQUENCE: 9
```

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

```
Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
            325                 330                 335

Glu Ala Leu Glu Glu Arg Pro Ala Val Met Thr Ser Pro Leu Tyr Leu
        340                 345                 350

Glu Asp Lys Thr His Thr Cys Pro Pro Cys Pro Ala Pro Glu Leu Leu
    355                 360                 365

Gly Gly Pro Ser Val Phe Leu Phe Pro Pro Lys Pro Lys Asp Thr Leu
370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
            405                 410                 415

Val His Asn Ala Lys Thr Lys Pro Arg Glu Glu Gln Tyr Asn Ser Thr
        420                 425                 430

Tyr Arg Val Val Ser Val Leu Thr Val Leu His Gln Asp Trp Leu Asn
    435                 440                 445

Gly Lys Glu Tyr Lys Cys Lys Val Ser Asn Lys Ala Leu Pro Ala Pro
450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Asp Glu Leu Thr Lys Asn Gln Val
            485                 490                 495

Ser Leu Thr Cys Leu Val Lys Gly Phe Tyr Pro Ser Asp Ile Ala Val
        500                 505                 510

Glu Trp Glu Ser Asn Gly Gln Pro Glu Asn Asn Tyr Lys Thr Thr Pro
    515                 520                 525

Pro Val Leu Asp Ser Asp Gly Ser Phe Phe Leu Tyr Ser Lys Leu Thr
530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
            565                 570                 575

Ser Pro Gly Lys
            580

<210> SEQ ID NO 10
<211> LENGTH: 526
<212> TYPE: PRT
<213> ORGANISM: Artificial sequence
<220> FEATURE:
<223> OTHER INFORMATION: #13 fusion protein

<400> SEQUENCE: 10

Lys Asn Arg Thr Arg Ile Thr Gly Glu Glu Val Glu Val Gln Asp Ser
1               5                   10                  15

Val Pro Ala Asp Ser Gly Leu Tyr Ala Cys Val Thr Ser Ser Pro Ser
            20                  25                  30

Gly Ser Asp Thr Thr Tyr Phe Ser Val Asn Val Ser Asp Ala Leu Pro
        35                  40                  45

Ser Ser Glu Asp Asp Asp Asp Asp Ser Ser Ser Glu Glu Lys
    50                  55                  60

Glu Thr Asp Asn Thr Lys Pro Asn Pro Val Ala Pro Tyr Trp Thr Ser
65                  70                  75                  80
```

```
Pro Glu Lys Met Glu Lys Leu His Ala Val Pro Ala Ala Lys Thr
             85                  90                  95

Val Lys Phe Lys Cys Pro Ser Ser Gly Thr Pro Asn Pro Thr Leu Arg
        100                 105                 110

Trp Leu Lys Asn Gly Lys Glu Phe Lys Pro Asp His Arg Ile Gly Gly
            115                 120                 125

Tyr Lys Val Arg Tyr Ala Thr Trp Ser Ile Ile Met Asp Ser Val Val
    130                 135                 140

Pro Ser Asp Lys Gly Asn Tyr Thr Cys Ile Val Glu Asn Glu Tyr Gly
145                 150                 155                 160

Ser Ile Asn His Thr Tyr Gln Leu Asp Val Val Glu Arg Ser Pro His
                165                 170                 175

Arg Pro Ile Leu Gln Ala Gly Leu Pro Ala Asn Lys Thr Val Ala Leu
                180                 185                 190

Gly Ser Asn Val Glu Phe Met Cys Lys Val Tyr Ser Asp Pro Gln Pro
            195                 200                 205

His Ile Gln Trp Leu Lys His Ile Glu Val Asn Gly Ser Lys Ile Gly
    210                 215                 220

Pro Asp Asn Leu Pro Tyr Val Gln Ile Leu Lys Thr Ala Gly Val Asn
225                 230                 235                 240

Thr Thr Asp Lys Glu Met Glu Val Leu His Leu Arg Asn Val Ser Phe
                245                 250                 255

Glu Asp Ala Gly Glu Tyr Thr Cys Leu Ala Gly Asn Ser Ile Gly Leu
                260                 265                 270

Ser His His Ser Ala Trp Leu Thr Val Leu Glu Ala Leu Glu Glu Arg
            275                 280                 285

Pro Ala Val Met Thr Ser Pro Leu Tyr Leu Glu Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
                340                 345                 350

Lys Phe Asn Trp Tyr Val Asp Gly Val Glu Val His Asn Ala Lys Thr
            355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
                420                 425                 430

Ser Arg Asp Glu Leu Thr Lys Asn Gln Val Ser Leu Thr Cys Leu Val
            435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
```

```
                    500                 505                 510
Asn His Tyr Thr Gln Lys Ser Leu Ser Leu Ser Pro Gly Lys
        515                 520                 525

<210> SEQ ID NO 11
<211> LENGTH: 500
<212> TYPE: PRT
<213> ORGANISM: Artificial sequence
<220> FEATURE:
<223> OTHER INFORMATION: #22 fusion protein

<400> SEQUENCE: 11

Val Thr Ser Ser Pro Ser Gly Ser Asp Thr Thr Tyr Phe Ser Val Asn
1               5                   10                  15

Val Ser Asp Ala Leu Pro Ser Ser Glu Asp Asp Asp Asp Asp Asp Asp
            20                  25                  30

Ser Ser Ser Glu Glu Lys Glu Thr Asp Asn Thr Lys Pro Asn Pro Val
        35                  40                  45

Ala Pro Tyr Trp Thr Ser Pro Glu Lys Met Glu Lys Lys Leu His Ala
    50                  55                  60

Val Pro Ala Ala Lys Thr Val Lys Phe Lys Cys Pro Ser Ser Gly Thr
65                  70                  75                  80

Pro Asn Pro Thr Leu Arg Trp Leu Lys Asn Gly Lys Glu Phe Lys Pro
                85                  90                  95

Asp His Arg Ile Gly Gly Tyr Lys Val Arg Tyr Ala Thr Trp Ser Ile
            100                 105                 110

Ile Met Asp Ser Val Val Pro Ser Asp Lys Gly Asn Tyr Thr Cys Ile
        115                 120                 125

Val Glu Asn Glu Tyr Gly Ser Ile Asn His Thr Tyr Gln Leu Asp Val
    130                 135                 140

Val Glu Arg Ser Pro His Arg Pro Ile Leu Gln Ala Gly Leu Pro Ala
145                 150                 155                 160

Asn Lys Thr Val Ala Leu Gly Ser Asn Val Glu Phe Met Cys Lys Val
                165                 170                 175

Tyr Ser Asp Pro Gln Pro His Ile Gln Trp Leu Lys His Ile Glu Val
            180                 185                 190

Asn Gly Ser Lys Ile Gly Pro Asp Asn Leu Pro Tyr Val Gln Ile Leu
        195                 200                 205

Lys Thr Ala Gly Val Asn Thr Thr Asp Lys Glu Met Glu Val Leu His
    210                 215                 220

Leu Arg Asn Val Ser Phe Glu Asp Ala Gly Glu Tyr Thr Cys Leu Ala
225                 230                 235                 240

Gly Asn Ser Ile Gly Leu Ser His His Ser Ala Trp Leu Thr Val Leu
                245                 250                 255

Glu Ala Leu Glu Glu Arg Pro Ala Val Met Thr Ser Pro Leu Tyr Leu
            260                 265                 270

Glu Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
```

```
                     340                 345                 350
Tyr Arg Val Val Ser Val Leu Thr Val Leu His Gln Asp Trp Leu Asn
            355                 360                 365
Gly Lys Glu Tyr Lys Cys Lys Val Ser Asn Lys Ala Leu Pro Ala Pro
        370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Asp Glu Leu Thr Lys Asn Gln Val
                405                 410                 415
Ser Leu Thr Cys Leu Val Lys Gly Phe Tyr Pro Ser Asp Ile Ala Val
            420                 425                 430
Glu Trp Glu Ser Asn Gly Gln Pro Glu Asn Asn Tyr Lys Thr Thr Pro
        435                 440                 445
Pro Val Leu Asp Ser Asp Gly Ser Phe Phe Leu Tyr Ser Lys Leu Thr
    450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly Lys
            500

<210> SEQ ID NO 12
<211> LENGTH: 468
<212> TYPE: PRT
<213> ORGANISM: Artificial sequence
<220> FEATURE:
<223> OTHER INFORMATION: #23 fusion protein

<400> SEQUENCE: 12

Ser Ser Ser Glu Glu Lys Glu Thr Asp Asn Thr Lys Pro Asn Pro Val
1               5                   10                  15
Ala Pro Tyr Trp Thr Ser Pro Glu Lys Met Glu Lys Lys Leu His Ala
            20                  25                  30
Val Pro Ala Ala Lys Thr Val Lys Phe Lys Cys Pro Ser Ser Gly Thr
        35                  40                  45
Pro Asn Pro Thr Leu Arg Trp Leu Lys Asn Gly Lys Glu Phe Lys Pro
    50                  55                  60
Asp His Arg Ile Gly Gly Tyr Lys Val Arg Tyr Ala Thr Trp Ser Ile
65                  70                  75                  80
Ile Met Asp Ser Val Val Pro Ser Asp Lys Gly Asn Tyr Thr Cys Ile
                85                  90                  95
Val Glu Asn Glu Tyr Gly Ser Ile Asn His Thr Tyr Gln Leu Asp Val
            100                 105                 110
Val Glu Arg Ser Pro His Arg Pro Ile Leu Gln Ala Gly Leu Pro Ala
        115                 120                 125
Asn Lys Thr Val Ala Leu Gly Ser Asn Val Glu Phe Met Cys Lys Val
    130                 135                 140
Tyr Ser Asp Pro Gln Pro His Ile Gln Trp Leu Lys His Ile Glu Val
145                 150                 155                 160
Asn Gly Ser Lys Ile Gly Pro Asp Asn Leu Pro Tyr Val Gln Ile Leu
                165                 170                 175
Lys Thr Ala Gly Val Asn Thr Thr Asp Lys Glu Met Glu Val Leu His
            180                 185                 190
Leu Arg Asn Val Ser Phe Glu Asp Ala Gly Glu Tyr Thr Cys Leu Ala
```

```
                195                 200                 205
Gly Asn Ser Ile Gly Leu Ser His His Ser Ala Trp Leu Thr Val Leu
    210                 215                 220

Glu Ala Leu Glu Glu Arg Pro Ala Val Met Thr Ser Pro Leu Tyr Leu
225                 230                 235                 240

Glu Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 13
<211> LENGTH: 457
<212> TYPE: PRT
<213> ORGANISM: Artificial sequence
<220> FEATURE:
<223> OTHER INFORMATION: #26 fusion protein

<400> SEQUENCE: 13

Lys Pro Asn Pro Val Ala Pro Tyr Trp Thr Ser Pro Glu Lys Met Glu
1               5                   10                  15

Lys Lys Leu His Ala Val Pro Ala Ala Lys Thr Val Lys Phe Lys Cys
            20                  25                  30

Pro Ser Ser Gly Thr Pro Asn Pro Thr Leu Arg Trp Leu Lys Asn Gly
        35                  40                  45

Lys Glu Phe Lys Pro Asp His Arg Ile Gly Gly Tyr Lys Val Arg Tyr
    50                  55                  60

Ala Thr Trp Ser Ile Ile Met Asp Ser Val Val Pro Ser Asp Lys Gly
65                  70                  75                  80

Asn Tyr Thr Cys Ile Val Glu Asn Glu Tyr Gly Ser Ile Asn His Thr
```

```
                        85                  90                  95
Tyr Gln Leu Asp Val Val Glu Arg Ser Pro His Arg Pro Ile Leu Gln
            100                 105                 110

Ala Gly Leu Pro Ala Asn Lys Thr Val Ala Leu Gly Ser Asn Val Glu
        115                 120                 125

Phe Met Cys Lys Val Tyr Ser Asp Pro Gln Pro His Ile Gln Trp Leu
    130                 135                 140

Lys His Ile Glu Val Asn Gly Ser Lys Ile Gly Pro Asp Asn Leu Pro
145                 150                 155                 160

Tyr Val Gln Ile Leu Lys Thr Ala Gly Val Asn Thr Thr Asp Lys Glu
                165                 170                 175

Met Glu Val Leu His Leu Arg Asn Val Ser Phe Glu Asp Ala Gly Glu
            180                 185                 190

Tyr Thr Cys Leu Ala Gly Asn Ser Ile Gly Leu Ser His His Ser Ala
        195                 200                 205

Trp Leu Thr Val Leu Glu Ala Leu Glu Glu Arg Pro Ala Val Met Thr
    210                 215                 220

Ser Pro Leu Tyr Leu Glu Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 14
<211> LENGTH: 451
<212> TYPE: PRT
<213> ORGANISM: Artificial sequence
<220> FEATURE:
<223> OTHER INFORMATION: #29 fusion protein
```

-continued

```
<400> SEQUENCE: 14

Pro Tyr Trp Thr Ser Pro Glu Lys Met Glu Lys Lys Leu His Ala Val
1               5                   10                  15

Pro Ala Ala Lys Thr Val Lys Phe Lys Cys Pro Ser Ser Gly Thr Pro
            20                  25                  30

Asn Pro Thr Leu Arg Trp Leu Lys Asn Gly Lys Glu Phe Lys Pro Asp
        35                  40                  45

His Arg Ile Gly Gly Tyr Lys Val Arg Tyr Ala Thr Trp Ser Ile Ile
    50                  55                  60

Met Asp Ser Val Val Pro Ser Asp Lys Gly Asn Tyr Thr Cys Ile Val
65                  70                  75                  80

Glu Asn Glu Tyr Gly Ser Ile Asn His Thr Tyr Gln Leu Asp Val Val
                85                  90                  95

Glu Arg Ser Pro His Arg Pro Ile Leu Gln Ala Gly Leu Pro Ala Asn
            100                 105                 110

Lys Thr Val Ala Leu Gly Ser Asn Val Glu Phe Met Cys Lys Val Tyr
        115                 120                 125

Ser Asp Pro Gln Pro His Ile Gln Trp Leu Lys His Ile Glu Val Asn
130                 135                 140

Gly Ser Lys Ile Gly Pro Asp Asn Leu Pro Tyr Val Gln Ile Leu Lys
145                 150                 155                 160

Thr Ala Gly Val Asn Thr Thr Asp Lys Glu Met Glu Val Leu His Leu
                165                 170                 175

Arg Asn Val Ser Phe Glu Asp Ala Gly Glu Tyr Thr Cys Leu Ala Gly
            180                 185                 190

Asn Ser Ile Gly Leu Ser His His Ser Ala Trp Leu Thr Val Leu Glu
        195                 200                 205

Ala Leu Glu Glu Arg Pro Ala Val Met Thr Ser Pro Leu Tyr Leu Glu
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 15
<211> LENGTH: 446
<212> TYPE: PRT
<213> ORGANISM: Artificial sequence
<220> FEATURE:
<223> OTHER INFORMATION: #8 fusion protein

<400> SEQUENCE: 15

Pro Glu Lys Met Glu Lys Lys Leu His Ala Val Pro Ala Ala Lys Thr
1               5                   10                  15

Val Lys Phe Lys Cys Pro Ser Ser Gly Thr Pro Asn Pro Thr Leu Arg
            20                  25                  30

Trp Leu Lys Asn Gly Lys Glu Phe Lys Pro Asp His Arg Ile Gly Gly
        35                  40                  45

Tyr Lys Val Arg Tyr Ala Thr Trp Ser Ile Ile Met Asp Ser Val Val
    50                  55                  60

Pro Ser Asp Lys Gly Asn Tyr Thr Cys Ile Val Glu Asn Glu Tyr Gly
65              70                  75                  80

Ser Ile Asn His Thr Tyr Gln Leu Asp Val Val Glu Arg Ser Pro His
                85                  90                  95

Arg Pro Ile Leu Gln Ala Gly Leu Pro Ala Asn Lys Thr Val Ala Leu
            100                 105                 110

Gly Ser Asn Val Glu Phe Met Cys Lys Val Tyr Ser Asp Pro Gln Pro
        115                 120                 125

His Ile Gln Trp Leu Lys His Ile Glu Val Asn Gly Ser Lys Ile Gly
    130                 135                 140

Pro Asp Asn Leu Pro Tyr Val Gln Ile Leu Lys Thr Ala Gly Val Asn
145                 150                 155                 160

Thr Thr Asp Lys Glu Met Glu Val Leu His Leu Arg Asn Val Ser Phe
                165                 170                 175

Glu Asp Ala Gly Glu Tyr Thr Cys Leu Ala Gly Asn Ser Ile Gly Leu
            180                 185                 190

Ser His His Ser Ala Trp Leu Thr Val Leu Glu Ala Leu Glu Glu Arg
        195                 200                 205

Pro Ala Val Met Thr Ser Pro Leu Tyr Leu Glu Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 16
<211> LENGTH: 1743
<212> TYPE: DNA
<213> ORGANISM: Artificial sequence
<220> FEATURE:
<223> OTHER INFORMATION: nucleotide sequence of #19 fusion protein

<400> SEQUENCE: 16
aggccgtccc cgaccttgcc tgaacaagcc cagccctggg gagcccctgt ggaagtggag      60
tccttcctgg tccaccccgg tgacctgcta cagcttcgct gtcggctgcg ggacgatgtg     120
cagagcatca actggctgcg ggacggggtg cagctggcgg aaagcaatcg cacccgcatc     180
acaggggagg aggtggaggt gcaggactcc gtgcccgcag actccggcct ctatgcttgc     240
gtaaccagca gccctcgggg cagtgacacc acctacttct ccgtcaatgt ttcagatgct     300
ctcccctcct cggaggatga tgatgatgat gatgactcct cttcagagga gaaagaaaca     360
gataacacca aaccaaaccc cgtagctcca tattggacat ccccagaaaa gatggaaaag     420
aaattgcatg cagtgccggc tgccaagaca gtgaagttca atgcccttc cagtgggacc     480 ccaaacccca cactgcgctg gttgaaaaat ggcaagaat tcaaacctga ccacagaatt     540
ggaggctaca aggtccgtta tgccacctgg agcatcataa tggactctgt ggtgccctct     600
gacaagggca actacacctg cattgtggag aatgagtacg gcagcatcaa ccacacatac     660
cagctggatg tcgtggagcg gtcccctcac cggcccatcc tgcaagcagg gttgcccgcc     720
aacaaaacag tggccctggg tagcaacgtg gagttcatgt gtaaggtgta cagtgacccg     780
cagccgcaca tccagtggct aaagcacatc gaggtgaatg gagcaagat ggcccagac     840 aacctgcctt atgtccagat cttgaagact gctggagtta ataccaccga caaagagatg     900
gaggtgcttc acttaagaaa tgtctccttt gaggacgcag gggagtatac gtgcttggcg     960
ggtaactcta tcggactctc ccatcactct gcatggttga ccgttctgga agccctggaa    1020
gagaggccgg cagtgatgac ctcgcccctg tacctggagg acaaaactca cacatgccca    1080
ccgtgcccag cacctgaact cctgggggga ccgtcagtct tcctcttccc cccaaaaccc    1140
aaggacaccc tcatgatctc ccggaccct gaggtcacat gcgtggtggt ggacgtgagc    1200
cacgaagacc ctgaggtcaa gttcaactgg tacgtgacg gcgtggaggt gcataatgcc    1260
aagacaaagc cgcggggagga gcagtacaac agcacgtacc gtgtggtcag cgtcctcacc    1320
```

| | |
|---|---|
| gtcctgcacc aggactggct gaatggcaag gagtacaagt gcaaggtctc caacaaagcc | 1380 |
| ctcccagccc ccatcgagaa aaccatctcc aaagccaaag gcagccccg agaaccacag | 1440 |
| gtgtacaccc tgcccccatc ccgggatgag ctgaccaaga accaggtcag cctgacctgc | 1500 |
| ctggtcaaag gcttctatcc cagcgacatc gccgtggagt gggagagcaa tgggcagccg | 1560 |
| gagaacaact acaagaccac gcctcccgtg ctggactccg acggctcctt cttcctctac | 1620 |
| agcaagctca ccgtggacaa gagcaggtgg cagcagggga acgtcttctc atgctccgtg | 1680 |
| atgcatgagg ctctgcacaa ccactacacg cagaagagcc tctccctgtc tccgggtaaa | 1740 |
| tga | 1743 |

```
<210> SEQ ID NO 17
<211> LENGTH: 1581
<212> TYPE: DNA
<213> ORGANISM: Artificial sequence
<220> FEATURE:
<223> OTHER INFORMATION: nucleotide sequence of #13 fusion protein

<400> SEQUENCE: 17
```

| | |
|---|---|
| aaaaatcgca cccgcatcac aggggaggag gtggaggtgc aggactccgt gcccgcagac | 60 |
| tccggcctct atgcttgcgt aaccagcagc ccctcgggca gtgacaccac ctacttctcc | 120 |
| gtcaatgttt cagatgctct cccctcctcg gaggatgatg atgatgatga tgactcctct | 180 |
| tcagaggaga agaaacaga taacaccaaa ccaaaccccg tagctccata ttggacatcc | 240 |
| ccagaaaaga tggaaaagaa attgcatgca gtgccggctg ccaagacagt gaagttcaaa | 300 |
| tgcccttcca gtgggacccc aaaccccaca ctgcgctggt tgaaaaatgg caaagaattc | 360 |
| aaacctgacc acagaattgg aggctacaag gtccgttatg ccacctggag catcataatg | 420 |
| gactctgtgg tgccctctga aagggcaac tacacctgca ttgtggagaa tgagtacggc | 480 |
| agcatcaacc acacatacca gctggatgtc gtggagcggt cccctcaccg gcccatcctg | 540 |
| caagcagggt tgcccgccaa caaaacagtg gccctgggta gcaacgtgga gttcatgtgt | 600 |
| aaggtgtaca gtgacccgca gccgcacatc cagtggctaa agcacatcga ggtgaatggg | 660 |
| agcaagattg gccagacaa cctgccttat gtccagatct tgaagactgc tggagttaat | 720 |
| accaccgaca agagatgga ggtgcttcac ttaagaaatg tctcctttga ggacgcaggg | 780 |
| gagtatacgt gcttggcggg taactctatc ggactctccc atcactctgc atggttgacc | 840 |
| gttctggaag ccctggaaga gaggccggca gtgatgacct cgcccctgta cctggaggac | 900 |
| aaaactcaca catgcccacc gtgcccagca cctgaactcc tggggggacc gtcagtcttc | 960 |
| ctcttccccc caaaacccaa ggacaccctc atgatctccc ggacccctga ggtcacatgc | 1020 |
| gtggtggtgg acgtgagcca cgaagaccct gaggtcaagt tcaactggta cgtggacggc | 1080 |
| gtggaggtgc ataatgccaa gacaaagccg cgggaggagc agtacaacag cacgtaccgt | 1140 |
| gtggtcagcg tcctcaccgt cctgcaccag gactggctga atggcaagga gtacaagtgc | 1200 |
| aaggtctcca acaaagccct cccagccccc atcgagaaaa ccatctccaa agccaaaggg | 1260 |
| cagccccgag aaccacaggt gtacaccctg cccccatccc gggatgagct gaccaagaac | 1320 |
| caggtcagcc tgacctgcct ggtcaaaggc ttctatccca gcgacatcgc cgtggagtgg | 1380 |
| gagagcaatg ggcagccgga gaacaactac aagaccacgc ctcccgtgct ggactccgac | 1440 |
| ggctccttct tcctctacag caagctcacc gtggacaaga gcaggtggca gcaggggaac | 1500 |
| gtcttctcat gctccgtgat gcatgaggct ctgcacaacc actacacgca gaagagcctc | 1560 |
| tccctgtctc cgggtaaatg a | 1581 |

```
<210> SEQ ID NO 18
<211> LENGTH: 1503
<212> TYPE: DNA
<213> ORGANISM: Artificial sequence
<220> FEATURE:
<223> OTHER INFORMATION: nucleotide sequence of #22 fusion protein

<400> SEQUENCE: 18
gtaaccagca gccccctcggg cagtgacacc acctacttct ccgtcaatgt ttcagatgct      60
ctcccctcct cggaggatga tgatgatgat gatgactcct cttcagagga gaaagaaaca     120
gataacacca aaccaaaccc cgtagctcca tattggacat ccccagaaaa gatggaaaag     180
aaattgcatg cagtgccggc tgccaagaca gtgaagttca atgcccttc cagtgggacc      240 ccaaacccca cactgcgctg gttgaaaaat ggcaaagaat caaacctga ccacagaatt      300 ggaggctaca aggtccgtta tgccacctgg agcatcataa tggactctgt ggtgccctct     360
gacaagggca actacacctg cattgtggag aatgagtacg gcagcatcaa ccacacatac     420
cagctggatg tcgtggagcg gtcccctcac cggcccatcc tgcaagcagg gttgcccgcc     480
aacaaaacag tgcccctggg tagcaacgtg gagttcatgt gtaaggtgta cagtgacccg     540
cagccgcaca tccagtggct aaagcacatc gaggtgaatg ggagcaagat tggcccagac     600
aacctgcctt atgtccagat cttgaagact gctggagtta ataccaccga caaagagatg     660
gaggtgcttc acttaagaaa tgtctccttt gaggacgcag gggagtatac gtgcttggcg     720
ggtaactcta tcggactctc ccatcactct gcatggttga ccgttctgga agccctggaa     780
gagaggccgg cagtgatgac ctcgcccctg tacctggagg acaaaactca cacatgccca     840
ccgtgcccag cacctgaact cctggggggga ccgtcagtct tcctcttccc cccaaaaccc     900
aaggacaccc tcatgatctc ccggacccct gaggtcacat gcgtggtggt ggacgtgagc     960
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag ggcagccccg agaaccacag    1200
gtgtacaccc tgcccccatc ccgggatgag ctgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggtaaa    1500
tga                                                                  1503

<210> SEQ ID NO 19
<211> LENGTH: 1407
<212> TYPE: DNA
<213> ORGANISM: Artificial sequence
<220> FEATURE:
<223> OTHER INFORMATION: nucleotide sequence of #23 fusion protein

<400> SEQUENCE: 19
tcctcttcag aggagaaaga aacagataac accaaaccaa ccccgtagc tccatattgg       60 acatccccag aaaagatgga aaagaaattg catgcagtgc cggctgccaa gacagtgaag     120
ttcaaatgcc cttccagtgg gaccccaaac cccacactgc gctggttgaa aaatggcaaa     180
```

| | |
|---|---|
| gaattcaaac ctgaccacag aattggaggc tacaaggtcc gttatgccac ctggagcatc | 240 |
| ataatggact ctgtggtgcc ctctgacaag ggcaactaca cctgcattgt ggagaatgag | 300 |
| tacggcagca tcaaccacac ataccagctg gatgtcgtgg agcggtcccc tcaccggccc | 360 |
| atcctgcaag cagggttgcc cgccaacaaa acagtggccc tgggtagcaa cgtggagttc | 420 |
| atgtgtaagg tgtacagtga cccgcagccg cacatccagt ggctaaagca catcgaggtg | 480 |
| aatgggagca agattggccc agacaacctg ccttatgtcc agatcttgaa gactgctgga | 540 |
| gttaatacca ccgacaaaga gatggaggtg cttcacttaa gaaatgtctc ctttgaggac | 600 |
| gcaggggagt atacgtgctt ggcgggtaac tctatcggac tctcccatca ctctgcatgg | 660 |
| ttgaccgttc tggaagccct ggaagagagg ccggcagtga tgacctcgcc cctgtacctg | 720 |
| gaggacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca aagccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaatga | 1407 |

<210> SEQ ID NO 20
<211> LENGTH: 1374
<212> TYPE: DNA
<213> ORGANISM: Artificial sequence
<220> FEATURE:
<223> OTHER INFORMATION: nucleotide sequence of #26 fusion protein

<400> SEQUENCE: 20

| | |
|---|---|
| aaacctaacc ccgtagctcc atattggaca tccccagaaa agatggaaaa gaaattgcat | 60 |
| gcagtgccgg ctgccaagac agtgaagttc aaatgcccct ccagtgggac cccaaacccc | 120 |
| acactgcgct ggttgaaaaa tgcaaagaa ttcaaacctg accacagaat tggaggctac | 180 |
| aaggtccgtt atgccacctg gagcatcata atggactctg tggtgccctc tgacaagggc | 240 |
| aactacacct gcattgtgga gaatgagtac ggcagcatca accacacata ccagctggat | 300 |
| gtcgtggagc ggtcccctca ccggcccatc ctgcaagcag ggttgcccgc caacaaaaca | 360 |
| gtggccctgg gtagcaacgt ggagttcatg tgtaaggtgt acagtgaccc gcagccgcac | 420 |
| atccagtggc taaagcacat cgaggtgaat gggagcaaga ttggcccaga caacctgcct | 480 |
| tatgtccaga tcttgaagac tgctggagtt aataccaccg acaaagagat ggaggtgctt | 540 |
| cacttaagaa atgtctcctt tgaggacgca ggggagtata cgtgcttggc gggtaactct | 600 |
| atcggactct cccatcactc tgcatggttg accgttctgg aagccctgga agagaggccg | 660 |
| gcagtgatga cctcgcccct gtacctggag gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |

```
cctgaggtca agttcaactg gtacgtggac ggcgtggagg tgcataatgc caagacaaag      900
ccgcgggagg agcagtacaa cagcacgtac cgtgtggtca gcgtcctcac cgtcctgcac      960
caggactggc tgaatggcaa ggagtacaag tgcaaggtct ccaacaaagc cctcccagcc     1020
cccatcgaga aaaccatctc caaagccaaa gggcagcccc gagaaccaca ggtgtacacc     1080
ctgcccccat cccgggatga gctgaccaag aaccaggtca gcctgacctg cctggtcaaa     1140
ggcttctatc ccagcgacat cgccgtggag tgggagagca atgggcagcc ggagaacaac     1200
tacaagacca cgcctcccgt gctggactcc gacggctcct tcttcctcta cagcaagctc     1260
accgtggaca agagcaggtg gcagcagggg aacgtcttct catgctccgt gatgcatgag     1320
gctctgcaca accactacac gcagaagagc ctctccctgt ctccgggtaa atga           1374
```

<210> SEQ ID NO 21
<211> LENGTH: 1356
<212> TYPE: DNA
<213> ORGANISM: Artificial sequence
<220> FEATURE:
<223> OTHER INFORMATION: nucleotide sequence of #29 fusion protein

<400> SEQUENCE: 21

```
ccatattgga catccccaga aaagatggaa aagaaattgc atgcagtgcc ggctgccaag       60
acagtgaagt tcaaatgccc ttccagtggg accccaaacc ccacactgcg ctggttgaaa      120
aatggcaaag aattcaaacc tgaccacaga attggaggct acaaggtccg ttatgccacc      180
tggagcatca taatggactc tgtggtgccc tctgacaagg gcaactacac ctgcattgtg      240
gagaatgagt acggcagcat caaccacaca taccagctgg atgtcgtgga gcggtcccct      300
caccggccca tcctgcaagc agggttgccc gccaacaaaa cagtggccct gggtagcaac      360
gtggagttca tgtgtaaggt gtacagtgac ccgcagccgc acatccagtg gctaaagcac      420
atcgaggtga atgggagcaa gattggccca gacaacctgc cttatgtcca gatcttgaag      480
actgctggag ttaataccac cgacaaagag atggaggtgc ttcacttaag aaatgtctcc      540
tttgaggacg caggggagta acgtgcttg gcgggtaact ctatcggact ctcccatcac      600
tctgcatggt tgaccgttct ggaagccctg aagagaggc cggcagtgat gacctcgccc      660
ctgtacctgg aggacaaaac tcacacatgc ccaccgtgcc cagcacctga actcctgggg      720
ggaccgtcag tcttcctctt ccccccaaaa cccaaggaca cctcatgat ctcccggacc      780 cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcccag cccccatcga aaaaccatc     1020 tccaaagcca aagggcagcc ccgagaacca ggtgtaca ccctgccccc atcccgggat     1080
gagctgacca gaaccaggt cagcctgacc tgcctggtca aaggcttcta tcccagcgac     1140
atcgccgtgg agtgggagag caatgggcag ccggagaaca actacaagac cacgcctccc     1200
gtgctggact ccgacggctc cttcttcctc tacagcaagc tcaccgtgga caagagcagg     1260
tggcagcagg ggaacgtctt ctcatgctcc gtgatgcatg aggctctgca caaccactac     1320
acgcagaaga gcctctccct gtctccgggt aaatga                                1356
```

<210> SEQ ID NO 22
<211> LENGTH: 1341
<212> TYPE: DNA

<213> ORGANISM: Artificial sequence
<220> FEATURE:
<223> OTHER INFORMATION: nucleotide sequence of #8 fusion protein

<400> SEQUENCE: 22

```
ccagaaaaga tggaaaagaa attgcatgca gtgccggctg ccaagacagt gaagttcaaa      60
tgcccttcca gtgggacccc aaaccccaca ctgcgctggt tgaaaatgg caaagaattc     120
aaacctgacc acagaattgg aggctacaag gtccgttatg ccacctggag catcataatg    180
gactctgtgg tgccctctga caagggcaac tacacctgca ttgtggagaa tgagtacggc    240
agcatcaacc acacatacca gctggatgtc gtggagcggt ccctcaccg gcccatcctg    300
caagcagggt tgcccgccaa caaaacagtg ccctgggta gcaacgtgga gttcatgtgt    360
aaggtgtaca gtgaccccgca gccgcacatc cagtggctaa agcacatcga ggtgaatggg    420
agcaagattg gcccagacaa cctgccttat gtccagatct gaagactgc tggagttaat     480
accaccgaca aagagatgga ggtgcttcac ttaagaaatg tctcctttga ggacgcaggg    540
gagtatacgt gcttggcggg taactctatc ggactctccc atcactctgc atggttgacc    600
gttctggaag ccctggaaga gaggccggca gtgatgacct cgcccctgta cctggaggac    660
aaaactcaca catgcccacc gtgcccagca cctgaactcc tggggggacc gtcagtcttc    720
ctcttccccc caaaacccaa ggacaccctc atgatctccc ggaccctga ggtcacatgc     780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaatg a                                             1341
```

<210> SEQ ID NO 23
<211> LENGTH: 78
<212> TYPE: DNA
<213> ORGANISM: Homo sapiens
<220> FEATURE:
<221> NAME/KEY: misc_feature
<222> LOCATION: (1)..(78)
<223> OTHER INFORMATION: DNA sequence of VEGFR1 signal peptide

<400> SEQUENCE: 23

```
atggtcagct actgggacac cggggtcctg ctgtgcgcgc tgctcagctg tctgcttctc      60
acaggatcta gttccgga                                                   78
```

<210> SEQ ID NO 24
<211> LENGTH: 32
<212> TYPE: DNA
<213> ORGANISM: Artificial sequence
<220> FEATURE:
<223> OTHER INFORMATION: forward primer DNA sequence of #19 fusion
      protein

<400> SEQUENCE: 24
tagttccgga aggccgtccc cgaccttgcc tg                                          32

<210> SEQ ID NO 25
<211> LENGTH: 32
<212> TYPE: DNA
<213> ORGANISM: Artificial sequence
<220> FEATURE:
<223> OTHER INFORMATION: forward primer of DNA sequence of #13 fusion
      protein

<400> SEQUENCE: 25
tagttccgga aaaaatcgca cccgcatcac ag                                          32

<210> SEQ ID NO 26
<211> LENGTH: 31
<212> TYPE: DNA
<213> ORGANISM: Artificial sequence
<220> FEATURE:
<223> OTHER INFORMATION: forward primer DNA sequence of #22 fusion
      protein

<400> SEQUENCE: 26
tagttccgga gtaaccagca gccccctcggg c                                          31

<210> SEQ ID NO 27
<211> LENGTH: 33
<212> TYPE: DNA
<213> ORGANISM: Artificial sequence
<220> FEATURE:
<223> OTHER INFORMATION: forward primer DNA sequence of #23 fusion
      protein

<400> SEQUENCE: 27
tagttccgga tcctcttcag aggagaaaga aac                                         33

<210> SEQ ID NO 28
<211> LENGTH: 32
<212> TYPE: DNA
<213> ORGANISM: Artificial sequence
<220> FEATURE:
<223> OTHER INFORMATION: forward primer DNA sequence of #26 fusion
      protein

<400> SEQUENCE: 28
tagttccgga aaacctaacc ccgtagctcc at                                          32

<210> SEQ ID NO 29
<211> LENGTH: 34
<212> TYPE: DNA
<213> ORGANISM: Artificial sequence
<220> FEATURE:
<223> OTHER INFORMATION: forward primer DNA sequence of #29 fusion
      protein

<400> SEQUENCE: 29
tagttccgga ccatattgga catccccaga aaag                                        34

<210> SEQ ID NO 30
<211> LENGTH: 36
<212> TYPE: DNA
<213> ORGANISM: Artificial sequence
<220> FEATURE:
<223> OTHER INFORMATION: forward primer DNA sequence of #8 fusion
      protein

<400> SEQUENCE: 30
ctagctccgg accagaaaag atggaaaaga aattgc                                      36

```
<210> SEQ ID NO 31
<211> LENGTH: 30
<212> TYPE: DNA
<213> ORGANISM: Artificial sequence
<220> FEATURE:
<223> OTHER INFORMATION: reverse primer DNA sequence of FGFR1

<400> SEQUENCE: 31
gttttgtcct ccaggtacag gggcgaggtc                                       30

<210> SEQ ID NO 32
<211> LENGTH: 30
<212> TYPE: DNA
<213> ORGANISM: Artificial sequence
<220> FEATURE:
<223> OTHER INFORMATION: forward primer DNA sequence of human IgG Fc

<400> SEQUENCE: 32
ctgtacctgg aggacaaaac tcacacatgc                                       30

<210> SEQ ID NO 33
<211> LENGTH: 30
<212> TYPE: DNA
<213> ORGANISM: Artificial sequence
<220> FEATURE:
<223> OTHER INFORMATION: reverse primer DNA sequence of human IgG Fc

<400> SEQUENCE: 33
gatatctgca gtcatttacc cggagacagg                                       30
```